United States Patent [19]

Nakatsuka et al.

[11] Patent Number: 5,072,021

[45] Date of Patent: Dec. 10, 1991

[54] OPTICAL ACTIVE NAPHTHALENE DERIVATIVES

[75] Inventors: Masakatsu Nakatsuka; Tsutomu Nishizawa, both of Yokohama, Japan

[73] Assignee: Mitsui Toatsu Chemicals, Inc., Tokyo, Japan

[21] Appl. No.: 467,300

[22] Filed: Jan. 16, 1990

Related U.S. Application Data

[62] Division of Ser. No. 137,263, Dec. 23, 1987, abandoned.

[30] Foreign Application Priority Data

Dec. 26, 1986 [JP] Japan .................... 61-314148

[51] Int. Cl.$^5$ .................... C07C 69/76; C09K 19/32
[52] U.S. Cl. .................... 560/56; 252/299.01; 252/299.62
[58] Field of Search .................... 560/56; 252/299.62, 252/299.01

[56] References Cited

U.S. PATENT DOCUMENTS

| | | | |
|---|---|---|---|
| 3,925,237 | 12/1975 | Ross et al. | 252/299.62 |
| 4,113,647 | 9/1978 | Coates et al. | 252/299.62 |
| 4,261,651 | 4/1981 | Gray et al. | 252/299.62 |
| 4,261,652 | 4/1981 | Gray et al. | 252/299.62 |
| 4,291,948 | 9/1981 | Crossland et al. | 252/299.1 |
| 4,340,498 | 7/1982 | Sugimori | 252/299.62 |
| 4,357,078 | 11/1982 | Carr et al. | 252/299.62 |
| 4,386,007 | 5/1983 | Krause et al. | 252/299.62 |
| 4,585,575 | 4/1986 | Sugimari et al. | 252/299.61 |
| 4,610,805 | 9/1986 | Schellenberger et al. | 252/299.62 |
| 4,613,209 | 9/1986 | Goodby et al. | 350/350.5 |
| 4,680,137 | 7/1987 | Isoyama et al. | 252/299.62 |
| 4,943,651 | 7/1990 | Nishiyama et al. | 560/56 |

FOREIGN PATENT DOCUMENTS

| | | | |
|---|---|---|---|
| 3515373 | 11/1986 | Fed. Rep. of Germany . | |
| 60-89449 | 5/1985 | Japan . | |
| 60-248790 | 12/1985 | Japan . | |
| 62-10045 | 1/1987 | Japan | 560/56 |
| 63-17847 | 1/1988 | Japan | 560/56 |
| 63-17848 | 1/1988 | Japan | 560/56 |
| 63-166850 | 7/1988 | Japan | 560/56 |
| 01128951 | 5/1989 | Japan | 560/56 |
| 1603075 | 11/1981 | United Kingdom | 560/56 |
| 2166754 | 5/1986 | United Kingdom . | |
| 87/01717 | 3/1987 | World Int. Prop. O. | 252/299.62 |
| 87/06577 | 11/1987 | World Int. Prop. O. | 560/56 |

OTHER PUBLICATIONS

Destrade et al., Mol. Cryst. Liq. Cryst., vol. 127, pp. 273-282 (1985).
Tinh et al., Mol. Cryst. Liq. Cryst., vol. 4(3-4), pp. 87-92 (Jan. 1987).
Demus (ed.), Flussigekristalle in Tabellen, pp. 234-242 (1976).
Demus (ed.), Flussigekristalle in Tabellen II, pp. 314-324 (1984).

Primary Examiner—John S. Maples
Assistant Examiner—Richard Treanor
Attorney, Agent, or Firm—Armstrong, Nikaido, Marmelstein, Kubovcik & Murray

[57] ABSTRACT

The present invention is directed to optically active compounds each containing a naphthalene skeleton, and to liquid crystal compositions which contain the aforesaid optical active compounds, these compositions being suitable for ferroelectric liquid crystal devices having excellent photostability and chemical stability and having a rapid responsivity. The compounds of the present invention are represented by the general formula

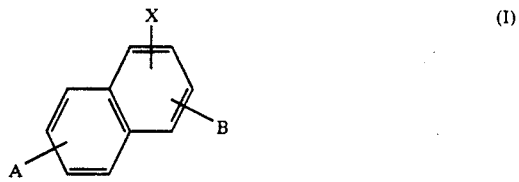

(I)

wherein X is a hydrogen atom, a halogen atom, a cyano group, an alkyl group or a methoxy group, the latter two groups each having 1 or 2 carbon atoms; and A and B are independently represented by following formula and at least one of them contains an asymmetric carbon atom

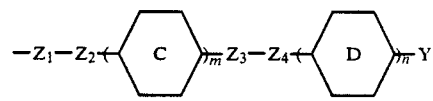

wherein C and D rings are independent and each of them is a 1,4-phenylene, 2,6-naphthylene, pyrimidine-2,5-diyl, trans-1,4-cyclohexylene, trans-1,3-dioxane-2,5-diyl, trans-1,3-oxathian-2,5-diyl, trans-1,3-dithian-2, 5-diyl or 1,3,2-dioxaborinane-2,5-diyl group; each of m and n is an integer of 0, 1 or 2; each of $Z_1$, $Z_2$, $Z_3$ and $Z_4$ is a bonding group of one or more selected from the group consisting of a single bond, —C(O)—, —O—, —CH$_2$—, —CH=N—, —N=CH—, —CH=CH—, —C≡C—, —N=N— and —N(O)=N—; and Y is a hydrogen atom, a halogen atom, a cyano group, a straight-chain or branched alkyl group or an alkenylalkyl group, the latter two groups each having 1 to 20 carbon atoms.

3 Claims, No Drawings

OPTICAL ACTIVE NAPHTHALENE DERIVATIVES

This application is a division of application Ser. No. 137,263 filed Dec. 23, 1987, now abandoned.

BACKGROUND OF THE INVENTION

1. Field of the Invention

The present invention relates to novel optically active compounds each containing a naphthalene skeleton and to liquid crystal compositions containing these compounds.

2. Description of the Prior Art

Presently, various kinds of liquid crystal display devices are used in many fields because the display operation of these elements is advantageously possible at a low voltage, in a low consumption of electric power and in a thin form and because they are photoreceptive and therefore conveniently they do not cause eyes of operators to get tired.

Above all, TN (twisted nematic) type display systems each employing a nematic liquid crystal are utilized in an extensive range. However, these display systems have the drawback that a response speed is low.

The advancement of the recent industrial technology strongly requires a rapid responsivity even in the field of the liquid crystal devices, and in reply to such a requirement, many attemps have been made by improving materials for the liquid crystals. As one example which can meet the above-mentioned demand, a display device has been already suggested in which a photoswitching phenomenon of a ferroelectric liquid crystal is utilized [Appl. Phys. Lett., 36, 899 (1980)]. As a liquid crystal phase for the ferroelectric liquid crystal, a chiral smectic C (SC*) phase is practically desirable, and some of the liquid crystal compounds showing the chiral smectic C phase have been heretofore investigated. Typical examples of these liquid crystal compounds are set forth in Table 1.

With regard to the ferroelectric liquid crystal compounds each having a naphthalene skeleton, Japanese Patent Laid-Open Publication No. 248,790/1985 suggests the possibility of the presence of their compounds but does not refer to concrete examples of such compounds. In this technical field, it cannot be presumed at all at present what skeleton in the compound causes the ferroelectric properties in the liquid crystal and what physical properties the ferroelectric liquid crystal has.

The inventors of the present application have found that liquid crystal compounds each having the naphthalene skeleton show remarkably excellent characteristics to compounds exemplified in the aforesaid patent publication, and the present invention has been completed on the basis of the found knowledge.

The conventional compounds in Table 1 may isomerize in a short period of time by light and may hydrolyze due to existent water, so that they come to have no liquid crystal phase any more at times. The compounds having such unstable factors are practically unpreferable as materials for various optical elements of displays and the like.

TABLE 1

| Chemical Structure | Phase Transition |
|---|---|
| 1. $C_{10}H_{21}O$—⟨Ph⟩—CH=H—⟨Ph⟩—CH=CH—C(=O)—$OCH_2\overset{*}{C}HC_2H_5$ (with $CH_3$ branch) | Crystal $\xrightarrow{76°\,C.}$ SC* $\xrightarrow{95°\,C.}$ SA $\xrightarrow{117°\,C.}$ / $\xrightarrow{63°\,C.}$ SH* isotropic liquid |
| 2. $C_6H_{13}O$—⟨Ph⟩—CH=N—⟨Ph⟩—CH=CH—C(=O)—$OCH_2\overset{*}{C}HCH_3$ (with Cl branch) | Crystal $\xrightarrow{60°\,C.}$ SH* $\xrightarrow{64°\,C.}$ SC* $\xrightarrow{78°\,C.}$ SA $\xrightarrow{135°\,C.}$ isopropic liquid |
| 3. $C_2H_5\overset{*}{C}H(CH_2)_5O$—⟨Ph⟩—CH=N—⟨Ph⟩—$C_8H_{17}$ (with $CH_3$ and OH substituents) | Crystal $\xrightarrow{12°\,C.}$ SC* $\xrightarrow{97°\,C.}$ isotropic liquid |

The compounds 1 and 2 above are described in J. Physique, 37, C3-129 (1976).
The compound 3 is described in Mol. Cryst. Liq. Cryst. Letters, 82, 61 (1982).

SUMMARY OF THE INVENTION

An object of the present invention is to provide compounds which are useful as novel ferroelectric liquid crystal materials or constitutional components of liquid crystal compositions having an excellent photostability and chemical stability.

Further, another object of the present invention is to provide liquid crystal compositions which are suitable for liquid crystal devices having a rapid responsivity.

The present invention is directed to optically active naphthalene derivatives represented by the general formula (I) and liquid crystal compositions each containing at least one of these derivatives:

(I) [naphthalene structure with substituent X at one position, and substituents A and B at the 2 and 6 positions]

wherein X is a hydrogen atom, a halogen atom, a cyano group, an alkyl group or methoxy group, latter two groups each having 1 or 2 carbon atoms; and A and B are independently represented by following formula and at least one of them contains an asymmetric carbon atom $$-Z_1-Z_2-\left(\phantom{x}C\phantom{x}\right)_{\overline{m}}-Z_3-Z_4-\left(\phantom{x}D\phantom{x}\right)_{\overline{m}}-Y$$

wherein C and D rings are independent and each of them is a 1,4-phenylene, 2,6-naphthylene, pyrimidine-2,5-diyl, trans-1,4-cyclohexylene, trans-1,3-dioxan-2,5-diyl, trans-1,3-oxathian-2,5-diyl, trans-1,3-dithian-2,5-diyl or 1,3,2-dioxaborinane-2,5-diyl group, these groups may be monosubstituted or multisubstituted by X; each of m and n is an integer of 0, 1 or 2; each of $Z_1$, $Z_2$, $Z_3$ and $Z_4$ is a bonding group of one or more selected from the group consisting of a single bond, —C(O)—, —O—, —CH$_2$—, —CH=N—, —N=CH—, —CH=CH—, —C≡C—, —N=N— and —N(O)-N—; and Y is a hydrogen atom, a halogen atom, a cyano group, a straight-chain or branched alkyl group or an alkenylalkyl group latter two groups each having 1 to 20 carbon atoms n which in its alkyl portion, one CH$_2$ group or two unadjacent CH$_2$ groups may be replaced with —O—, —C(O)—, —O—C(O)— or —C(O)—O— and one hydrogen atom may be replaced with a halogen atom, a cyano group or an alkoxyl group.

DESCRIPTION OF THE PREFERRED EMBODIMENTS

In order to solve the above-mentioned problems, the inventors of the present application have snythesized and investigated many liquid crystal compounds each containing an optically active group, and as a result, the present invention has been reached.

Most of the compounds having the above-mentioned general formula (I) can singly show a chiral smectic C phase which is important as a ferroelectric liquid crystal phase.

Some of the compounds having the general formula (I) show the smectic A phase and/or chiral nematic (cholesteric) phase only but do not exhibit any chiral smectic C phase, or some of them do not show the liquid crystal phase singly. Such compounds may be blended with other compounds having the general formula (I), other chiral smectic liquid crystal compounds, or other smectic liquid crystal compounds, so that they can be used as the liquid crystal compositions showing ferroelectric characteristics.

In the general formula (I), the naphthalene ring is substitutied by the groups A and B preferably at 1- and 4-positions, 1- and 5-positions or 2- and 6-positions thereof, more preferably at 2- and 6-positions thereof.

The group X in the general formula (I) is preferably a hydrogen atom, a halogen atom, a methyl group or a cyano group.

With regard to the general formula (I), each of $Z_1$, $Z_2$, $Z_3$ and $Z_4$ in the groups A and B can be selected from the group consisting of a single bond, —C(O)—, —O—, —CH$_2$—, —CH=N—, —N=CH—, —CH=CH—, —C≡C—, —N=N—and —N(O)=N—. However, taking photochemical or chemical stabilities into consideration, the single bond, —C(O)—, —O—or —CH$_2$—is preferable, and it is more preferred that each of the —$Z_1$—$Z_2$— and —$Z_3$—$Z_4$—groups is the single bond, —C(O)—O—, —O—C(O)—, —CH$_2$O—or —OCH$_2$—.

Each of the C and D rings can be optionally selected from the group consisting of 1,4-phenylene, 2,6-naphthylene, pyrimidine-2,5-diyl, trans-1,4-cyclohexylene, trans-1,3-dioxan-2, 5-diyl, trans-1,3-oxathian-2,5-diyl, trans-1,3-dithian-2,5-diyl, 1,3,2-dioxaborinane-2,5-diyl and groups in which hydrogen atom in each of these groups is monosubstituted or multisubstituted by X. However, these groups preferably are 1,4-phenylene, 2,6-naphthylene, pyrimidine-2,5-diyl, trans-1,4-cyclohexylene, 1,3,2-dioxaborinane-2,5-diyl and groups in which they are substituted by X, and more preferably they are 1,4-phenylene, 2,6-naphthylene, trans-1,4-cyclohexylene and groups in which they are substituted by X.

Each of m and n in the groups A and B is an integer of 0, 1 or 2, but preferably they are such balues as to satisfy the relation of m+n≦2.

In the compounds represented by the general formula (I), particularly preferable ones can be recited in general formulae as follows:

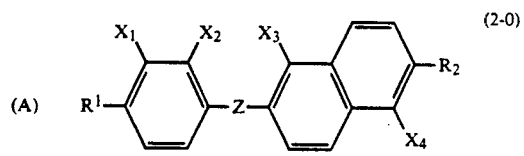

(A)  (2-0)

Concrete examples of this type can be enumerated in general formulae as follows:

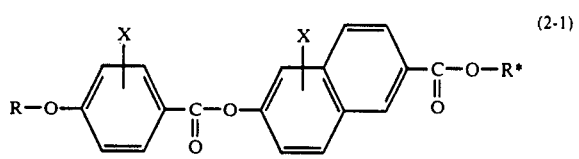

(2-1)

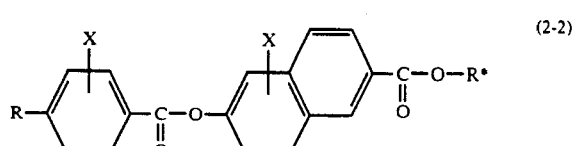

(2-2)

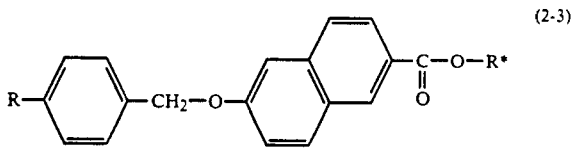

(2-3)

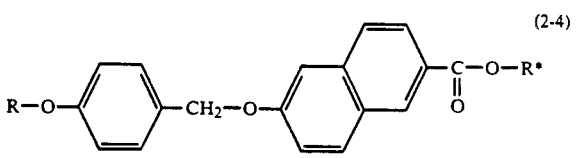

(2-4)

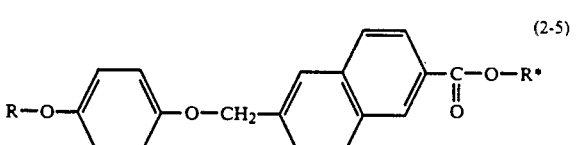

(2-5)

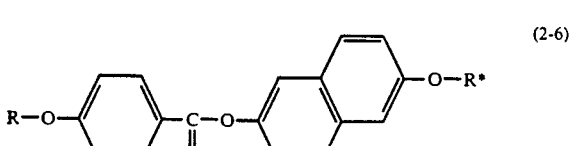

(2-6)

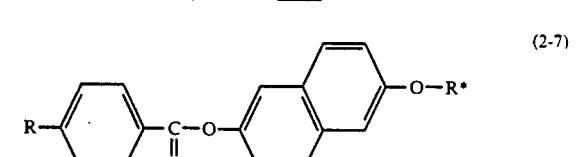

(2-7)

-continued
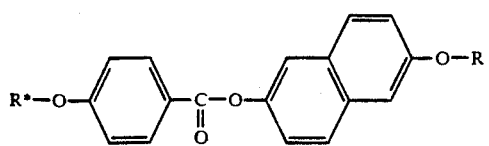 (2-8)
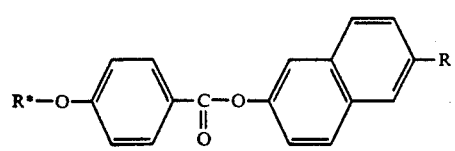 (2-9)
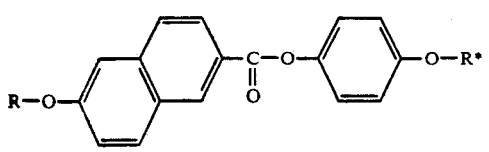 (2-10)
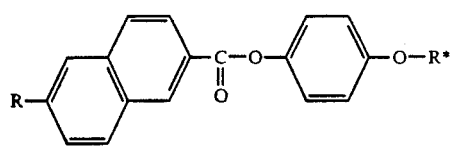 (2-11)
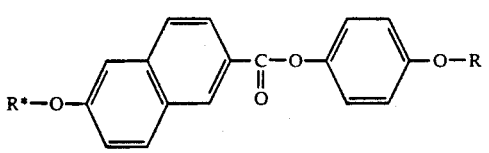 (2-12)
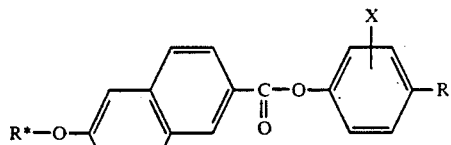 (2-13)
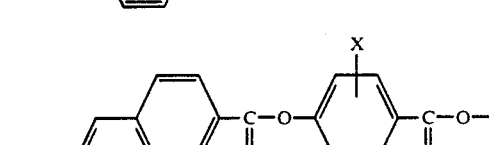 (2-14)
(B) 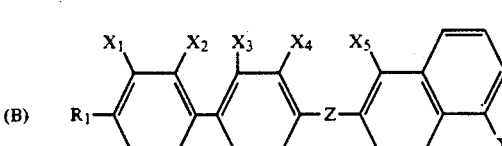 (3-0)
Concrete examples of this type can be enumerated in general formula as follows:
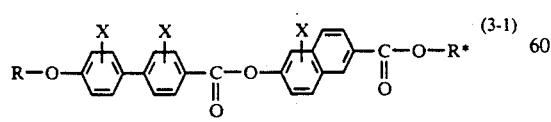 (3-1)
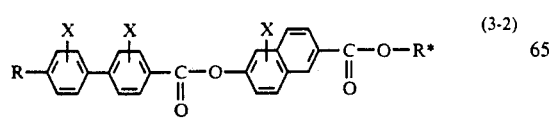 (3-2)
-continued
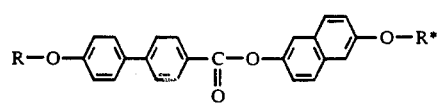 (3-3)
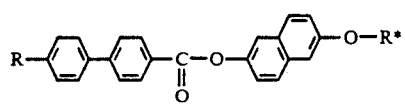 (3-4)
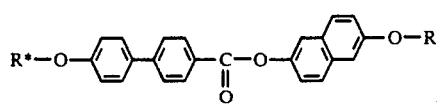 (3-5)
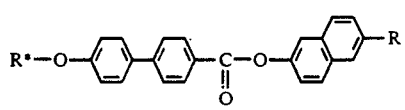 (3-6)
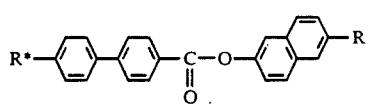 (3-7)
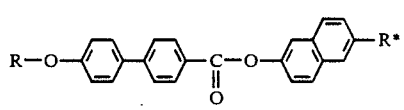 (3-8)
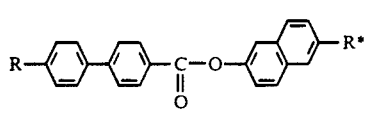 (3-9)
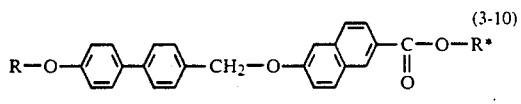 (3-10)
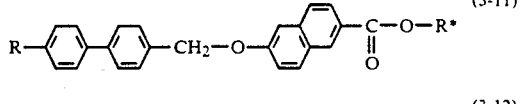 (3-11)
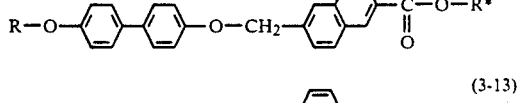 (3-12)
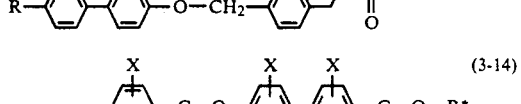 (3-13)
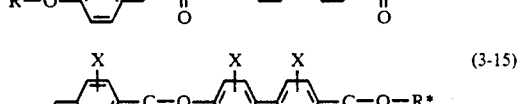 (3-14)
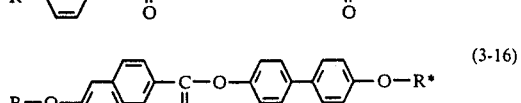 (3-15)
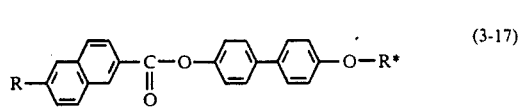 (3-16)
 (3-17)

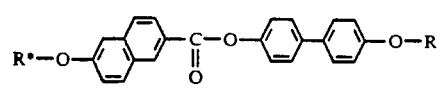 (3-18)
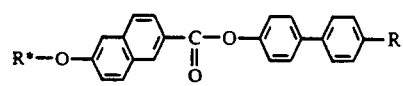 (3-19)
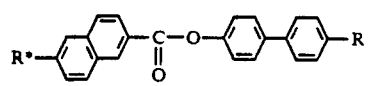 (3-20)
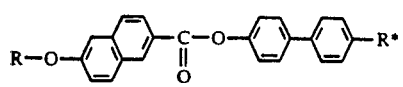 (3-21)
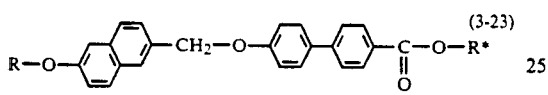 (3-22)
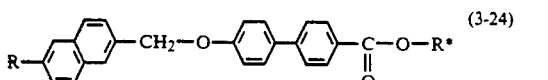 (3-23)
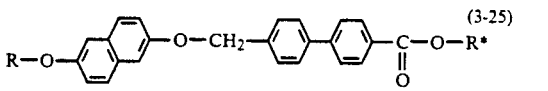 (3-24)
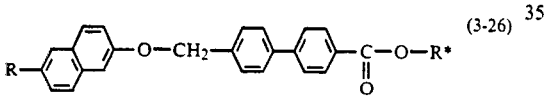 (3-25)
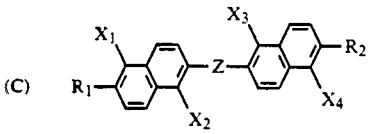 (3-26)
(C) 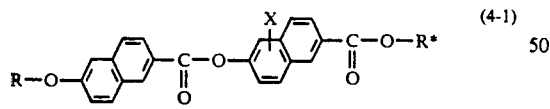 (4-0)
Concrete examples of this type can be enumerated in general formula as follows:
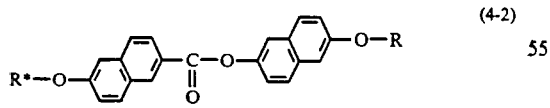 (4-1)
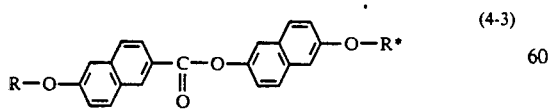 (4-2)
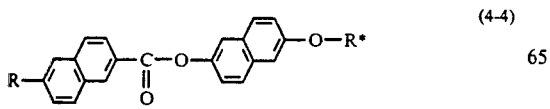 (4-3)
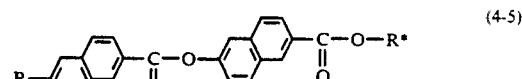 (4-4)
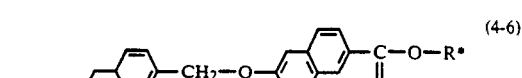 (4-5)
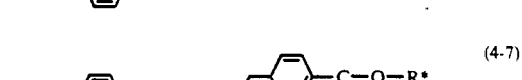 (4-6)
 (4-7)
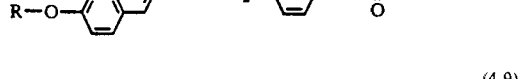 (4-8)
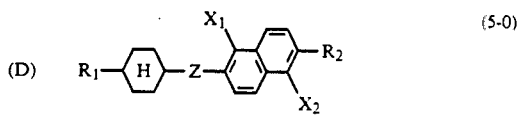 (4-9)
(D) 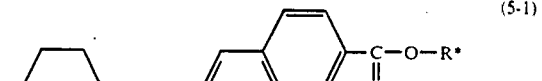 (5-0)
Concrete examples of this type can be enumerated in general formula as follows:
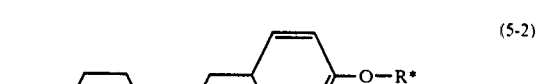 (5-1)
 (5-2)
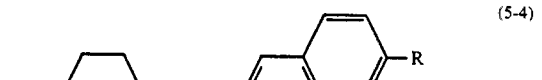 (5-3)
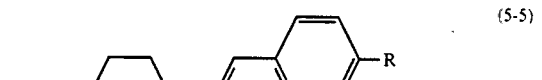 (5-4)
(5-5)

(5-6) 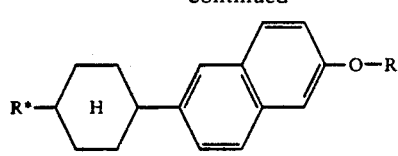

(5-7) 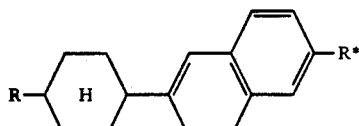

(E) 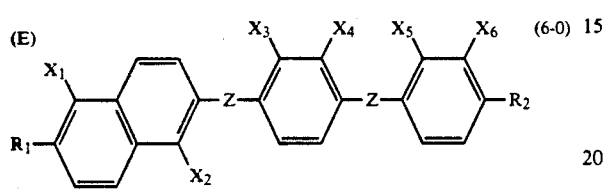

Concrete examples of this type can be enumerated in general formula as follows:

(6-1) 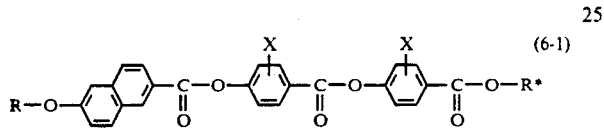

(6-2) 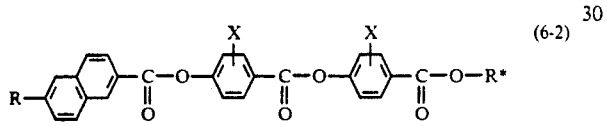

(6-3) 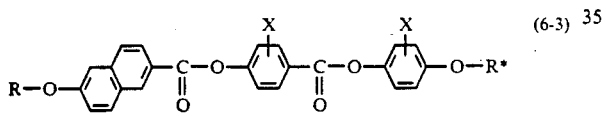

(6-4) 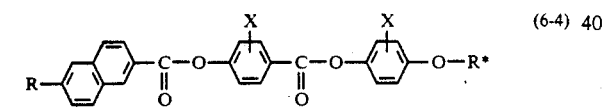

(6-5) 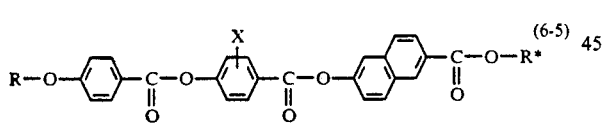

(6-6) 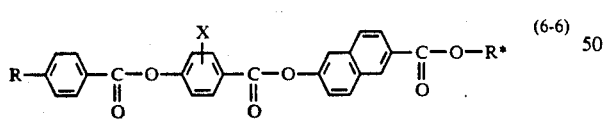

(6-7) 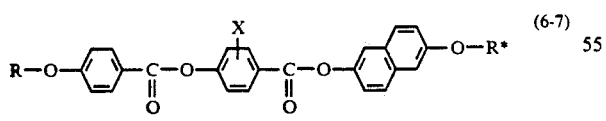

(6-8) 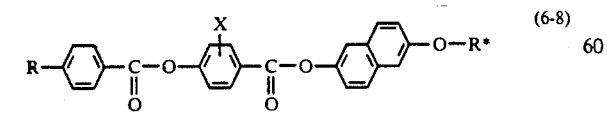

(F) (7-0) 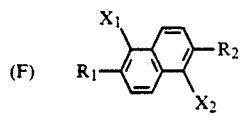

Concrete examples of this type can be enumerated in general formula as follows:

(7-1) 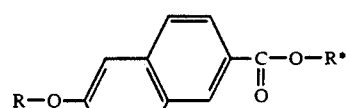

(7-2) 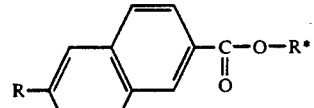

(7-3) 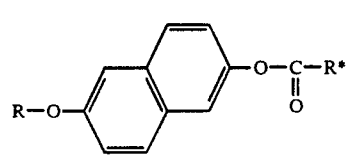

(7-4) 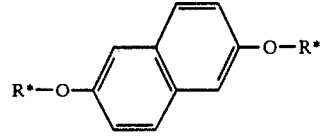

(7-5) 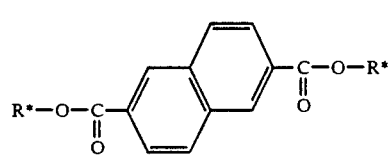

(7-6) 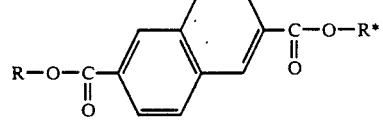

(7-7) 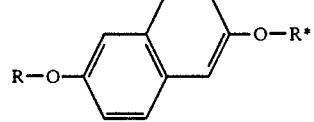

(7-8) 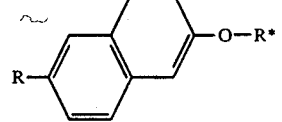

(7-9) 

In the above-mentioned formulae, $R_1$ and $R_2$ are independent and are respectively —R, —OR, —C(O)—OR— or —O—C(O)—R— and at least one of them contains an optically active group, in which groups R is a hydrogen atom, a halogen atom, a cyano group or a straight-chain or branched alkyl group, an alkoxyalkyl group, a halogenoalkyl group, a cyanoalkyl group, an alkenylalkyl group or an alkoxycarbonylalkyl group, latter six groups each having 1 to 20 carbon atoms; each of $X_1$ to $X_6$ is a hydrogen atom, a halogen atom, a methyl group or a cyano group; and Z is a single bond, —C(O)—O—, —O—C(O)—, —CH$_2$O— or —OCH$_2$—.

In the compound having the general formula (I), there exists at least one asymmetric carbon atom, but this atom preferably is present in the group Y of the group A and/or B. The group Y is a hydrogen atom, a halogen atom, a cyano group, a straight-chain or branched alkyl group or an alkenylalkyl group, the latter two groups each having 1 to 20 carbon atoms, and one CH$_2$ group or two unadjacent CH$_2$ groups in each of these alkyl groups may be substituted by —O—, —C(O)—, —O—C(O)— or —C(O)—O—, and one hydrogen atom in each of the alkyl groups may be substituted by a halogen atom, a cyano group or an alkoxyl group. Preferably, the group Y is a hydrogen atom, a halogen atom, a cyano group, a straight-chain or branched alkyl group or an alkenylalkyl group, the latter two groups each having 1 to 20 carbon atoms ( one CH$_2$ group or two unadjacent CH$_2$ groups in its alkyl portion may be substituted by —O—or —C-(O)—O—, and one hydrogen atom in the alkyl portion may be substituted by a halogen atom, a cyano group or an alkoxyl group).

As an asymmetric carbon source, all optically active materials are usable, but in particular, optically active alcohols and optically active carboxylic acids are useful as the starting materials.

Examples of the useful optically active alcohols include optically active 2-methylbutanol, optically active 3-methylpentanol, optically active 4-methylhexanol, optically active 5-methylheptanol, optically active 6-methyloctanol, optically active citronellol, optically active 3,7-dimethyloctanol, optically active 2-butanol, optically active 2-pentanol, optically active 2-hexanol, optically active 2-heptanol, optically active 2-octanol, optically active 2-nonanol, optically active 2-decanol, optically active 2-undecanol, optically active 2-dodecanol, optically active 2-methylpentanol, optically active 2-methylhexanol, optically active 2-alkyloxypropanol, optically active 3-alkyloxybutanol, optically active 3-alkyloxypentanol, optically active lactates, optically active 3-hydroxy-2-methylpropanoates, optically active 3-hydroxybutanoates, optically active 3-hydroxypentanoates, optically active 2-halogenopropanol, optically active 2-halogenobutanol, optically active 2-halogenopentanol, optically active 2-halogenohexanol, optically active 2-halogenoheptanol, optically active 2-halogenooctanol, optically active 2-halogenononanol, optically active 2-halogenodecanol, optically active 2-halogenoundecanol, optically active 2-halogenododecanol and optically active cyanoalkylcarbinol.

Examples of the useful optically active carboxylic acids include optically active 2-methylbutanoic acid, optically active 3-methylpentanoic acid, optically active 4-methylhexanoic acid, optically active 2-methylpentanoic acid, optically active 3,7-dimethyloctanoic acid, optically active 3-methyl-2-halogenopentanoic acid, optically active 4-methyl-2-halogenobutanoic acid, optically active 2-alkyloxypropanoic acid, optically active 3-alkyloxybutanoic acid and optically active 3-alkyloxypentanoic acid.

The liquid crystal composition according to the present invention may be constituted by combining two or more kinds of compounds regarding the present invention which are represented by the general formula (I), but it can also be prepared by joining the compound of the present invention to the following general formula (II).

The compound of the present invention having the general formula (I) and showing the chiral smectic C phase singly is preferably contained in a proportion of 5 wt % or more as a constitutional component in the liquid crystal composition. When this compound is present in the amount of 10 wt % or more in a known liquid crystal compound, a response speed of the known compound can be noticeably accelerated. The constitutional component showing no SC* phase is preferably present therein in a proportion of less than 50 wt %.

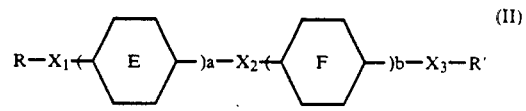

(II)

wherein E and F rings are independent and are

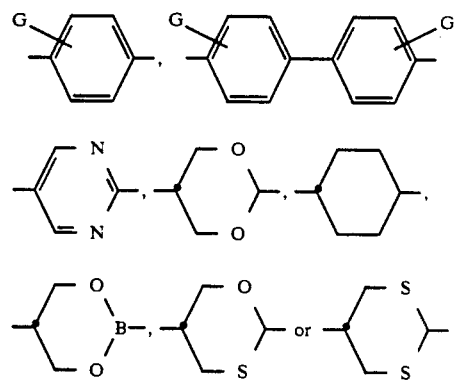

in which G is a hydrogen atom, a halogen atom, a cyano group or a methyl group; each of a and b is an integer of 0, 1 or 2; each of $X_1$, $X_2$ and $X_3$ is a single bond, —O—, —C(O)—O—, —O—C(O)—, —CH$_2$O—, —OCH$_2$— or —CH$_2$CH$_2$—; and each of R and R' is a hydrogen atom, a halogen atom, a cyano group, an alkyl group, an alkoxyl group, an optically active alkyl group, an optically active alkoxyl group, an optically active alkoxyalkyl group, an optically active alkenylalkyl group or an optically active halogenoalkyl group, the latter seven groups each having 1 to 20 carbon atoms.

The compound of the general formula (I) can be manufactured in accordance with the combination of known unit operations described in a literature (e.g. a standard academic literature such as "Methoden der Organischen Chemie" written by Houben Weil). In addition, known variations of the manufacturing methods which are not referred to in this specification can also be employed.

In the case that —Z$_1$—Z$_2$— of A and/or B in the formula (I) is —C(O)—O— and/or —O—C(O)—, raw materials preferably are combinations of compounds having formulae (III) and (IV)

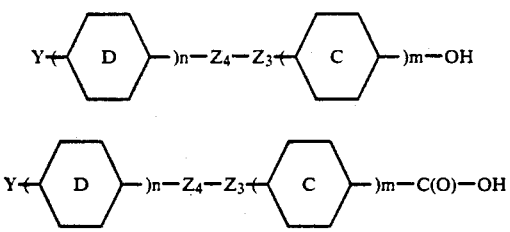

with compounds having formulae (V) to (VIII)

(VIII), or when a compound of the formula (IV) is combined with a compound of the formula (V) or (VII), the compound of the general formula I) can be prepared in accordance with an esterification process which is usually used. This process comprises, for example, the steps of first changing the carboxylic compound of the formula (IV), (VI or (VIII) into a reactive derivative such as a corresponding carboxylic acid halide (in particular, chloride or bromide) or carboxylic anhydride and afterward allowing the same to react with the compound of the formula (III), (V) or (VII).

In the case that $-Z_1-Z_2-$ of A and/or B in the formula (I) is $-CH_2O-$ and/or $-O-CH_2-$, raw materials preferably are combinations of compounds having formulae (III), (V) and (VII) with compounds having the following formulae (IX), (X) and (XI)

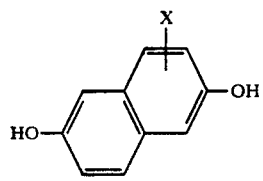

(V)

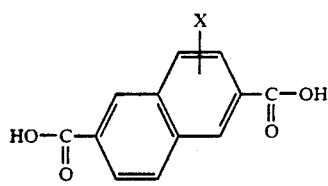

(VI)

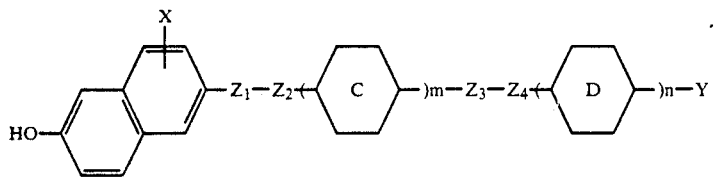

(VII)

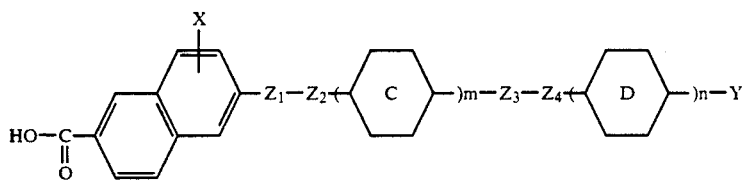

(VIII)

wherein X, $Z_1$, $Z_2$, $Z_3$, $Z_4$, rings C and D as well as Y are as defined above.

That is, when a compound of the formula (III) is combined with a compound of the formula (VI or

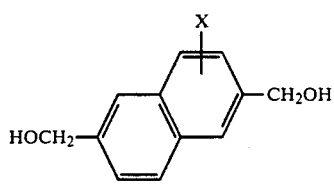

(IX)

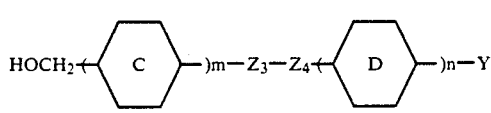

(X)

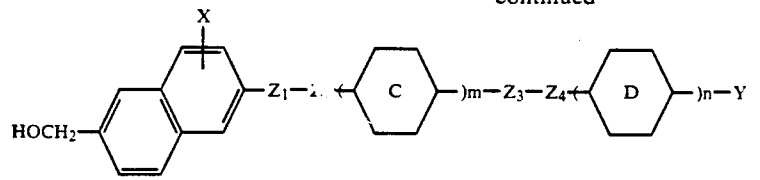

In the present invention, the reaction of a usual etherification can be used, and for example, the compound regarding the present invention can be prepared by reacting a hydroxyl compound with a reactive alkyl derivative such as a halide in the presence of a base (sodium hydroxide, potassium hydroxide, sodium hydride, potassium hydride or Table 2 sets forth typical examples of the compounds regarding the present invention.

As will be definite from examples given hereinafter, the present invention intends to provide optically active naphthalene derivative compounds represented by the general formula (I) and ferroelectric smectic liquid crystal compositions each containing at least one derivative compound mentioned above, whereby the present invention has an effect capable of providing rapidly responsive display elements having photostability and chemical stability.

TABLE 2

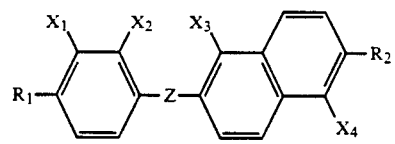

| Example Compound No. | $R^1$ | $X_1$ | $X_2$ | $X_3$ | $X_4$ | Z | $R_2$ |
|---|---|---|---|---|---|---|---|
| 1 | $CH_3O-$ | H | H | H | H | $-COO-$ | $-COOCH_2C^*H(CH_3)C_2H_5$ |
| 2 | $C_4H_9O-$ | H | H | H | H | " | " |
| 3 | $C_6H_{13}O-$ | H | H | H | H | " | " |
| 4 | $C_7H_{15}O-$ | H | H | H | H | " | " |
| 5 | $C_8H_{17}O-$ | H | H | H | H | " | " |
| 6 | $C_9H_{19}O-$ | H | H | H | H | " | " |
| 7 | $C_{10}H_{21}O-$ | H | H | H | H | " | " |
| 8 | $C_{11}H_{23}O-$ | H | H | H | H | " | " |
| 9 | $C_{12}H_{25}O-$ | H | H | H | H | " | " |
| 10 | $C_{13}H_{27}O-$ | H | H | H | H | " | " |
| 11 | $C_{14}H_{29}O-$ | H | H | H | H | " | " |
| 12 | $C_{15}H_{31}O-$ | H | H | H | H | " | " |
| 13 | $C_{16}H_{33}O-$ | H | H | H | H | " | " |
| 14 | $C_{18}H_{37}O-$ | H | H | H | H | " | " |
| 15 | $C_{20}H_{41}O-$ | H | H | H | H | " | " |
| 16 | $C_4H_9O-$ | F | H | H | H | " | " |
| 17 | $C_8H_{17}O-$ | F | H | H | H | " | " |
| 18 | $C_9H_{19}O-$ | F | H | H | H | " | " |
| 19 | $C_{10}H_{21}O-$ | F | H | H | H | " | " |
| 20 | $C_{12}H_{25}O-$ | F | H | H | H | " | " |
| 21 | $C_{16}H_{33}O-$ | F | H | H | H | " | " |
| 22 | $C_8H_{17}O-$ | Cl | H | H | H | " | " |
| 23 | $C_{10}H_{21}O-$ | Cl | H | H | H | " | " |
| 24 | $C_{12}H_{25}O-$ | Cl | H | H | H | $-COO-$ | $-COOCH_2C^*H(CH_3)C_2H_5$ |
| 25 | $C_8H_{17}O-$ | H | H | CN | H | " | " |
| 26 | $C_{10}H_{21}O-$ | Br | H | H | H | " | $-COO(CH_2)_2C^*H(CH_2)_3CHCH_3$ <br> $\quad\quad\quad\quad\quad\quad CH_3\quad\quad CH_3$ |
| 27 | $C_7H_{15}-$ | CN | H | H | H | "$-COOC^*H(CH_3)C_6H_{13}$ | " |
| 28 | $C_8H_{17}O-$ | H | F | H | H | " | " |
| 29 | $C_{10}H_{21}O-$ | F | H | H | H | " | " |
| 30 | $C_{12}H_{25}O-$ | F | H | H | H | " | $-COOC^*H(CH_3)C_6H_{13}$ |
| 31 | $C_9H_{19}O-$ | F | H | H | H | " | $-COOC^*H(CH_3)C_2H_5$ |
| 32 | $C_{12}H_{25}O-$ | F | H | H | H | " | " |
| 33 | $C_9H_{19}-$ | $OCH_3$ | H | H | H | " | " |
| 34 | $C_{10}H_{21}O-$ | F | H | H | H | " | $-COOC^*H(CH_3)C_3H_7$ |
| 35 | $C_{12}H_{25}O-$ | F | H | H | H | " | " |
| 36 | $C_6H_{13}O-$ | F | H | H | H | " | $-COO(CH_2)_2C^*H(CH_3)C_2H_5$ |
| 37 | $C_{11}H_{23}O-$ | F | H | H | H | " | " |
| 38 | $C_{10}H_{21}O-$ | F | H | H | H | " | $-COO(CH_2)_3C^*H(CH_3)C_2H_5$ |
| 39 | $C_{12}H_{25}O-$ | F | H | H | H | " | " |
| 40 | $C_{12}H_{25}O-$ | F | H | H | H | " | $-COO(CH_2)_4C^*H(CH_3)C_2H_5$ |
| 41 | $C_{12}H_{25}O-$ | F | H | H | H | " | $-COO(CH_2)_5C^*H(CH_3)C_2H_5$ |
| 42 | $C_{14}H_{29}O-$ | F | H | H | H | " | $-COO(CH_2)_5C^*H(CH_3)C_2H_5$ |
| 43 | $C_{10}H_{21}O-$ | H | H | Cl | H | " | $-COOCH_2C^*H(CH_3)C_2H_5$ |
| 44 | $C_{14}H_{29}O-$ | H | H | Cl | H | " | " |

TABLE 2-continued

| | | | | | | | |
|---|---|---|---|---|---|---|---|
| 45 | $C_{16}H_{33}O-$ | H | H | Cl | H | " | " |
| 46 | $C_8H_{17}O-$ | H | H | H | H | " | $-COO(CH_2)_2C^*H(CH_3)C_2H_5$ |
| 47 | $C_{10}H_{21}O-$ | H | H | H | H | " | " |
| 48 | $C_8H_{17}O-$ | H | H | H | H | $-COO-$ | $-COO(CH_2)_3C^*H(CH_3)C_2H_5$ |
| 49 | $C_9H_{19}O-$ | H | H | H | H | " | " |
| 50 | $C_{10}H_{21}O-$ | H | H | H | H | " | " |
| 51 | $C_{11}H_{23}O-$ | H | H | H | H | " | $-COO(CH_2)_3C^*H(CH_3)C_2H_5$ |
| 52 | $C_{12}H_{25}O-$ | H | H | H | H | " | " |
| 53 | $C_{13}H_{27}O-$ | H | H | H | H | " | " |
| 54 | $C_{14}H_{29}O-$ | H | H | H | H | " | " |
| 55 | $C_{15}H_{31}O-$ | H | H | H | H | " | " |
| 56 | $C_8H_{17}O-$ | H | H | H | H | " | $-COO(CH_2)_4C^*H(CH_3)C_2H_5$ |
| 57 | $C_9H_{19}O-$ | H | H | H | H | " | $-COO(CH_2)_5C^*H(CH_3)C_2H_5$ |
| 58 | $C_{10}H_{21}O-$ | H | H | H | H | " | " |
| 59 | $C_{12}H_{25}O-$ | H | H | H | H | " | " |
| 60 | $C_{10}H_{21}O-$ | H | H | H | H | " | $-COOCH_2C^*H(CH_3)C_3H_7$ |
| 61 | $C_{12}H_{25}O-$ | H | H | H | H | " | $-COOCH_2C^*H(CH_3)C_4H_9$ |
| 62 | $C_8H_{17}O-$ | H | H | H | H | " | $-COO(CH_2)_2C^*H(CH_2)_3CHCH_3$<br>$\quad\quad\quad\quad CH_3 \quad\quad CH_3$ |
| 63 | $C_{10}H_{21}O-$ | H | H | H | H | " | " |
| 64 | $C_{12}H_{25}O-$ | H | H | H | H | " | " |
| 65 | $C_4H_9O-$ | H | H | H | H | " | $-COOC^*H(CH_3)C_6H_{13}$ |
| 66 | $C_6H_{13}O-$ | H | H | H | H | " | " |
| 67 | $C_8H_{17}O-$ | H | H | H | H | " | " |
| 68 | $C_9H_{19}O-$ | H | H | H | H | " | " |
| 69 | $C_{10}H_{21}O-$ | H | H | H | H | " | " |
| 70 | $C_{11}H_{23}O-$ | H | H | H | H | " | " |
| 71 | $C_{12}H_{25}O-$ | H | H | H | H | " | " |
| 72 | $C_{14}H_{29}O-$ | H | H | H | H | $-COO-$ | $-COOC^*H(CH_3)C_6H_{13}$ |
| 73 | $C_{16}H_{33}O-$ | H | H | H | H | " | " |
| 74 | $C_{20}H_{41}O-$ | H | H | H | H | " | " |
| 75 | $C_{13}H_{27}O-$ | H | H | H | H | " | " |
| 76 | $C_4H_9O-$ | H | H | H | H | " | $-COOC^*H(CH_3)C_2H_5$ |
| 77 | $C_7H_{15}O-$ | H | H | H | H | " | " |
| 78 | $C_9H_{19}O-$ | H | H | H | H | " | " |
| 79 | $C_{10}H_{21}O-$ | H | H | H | H | " | " |
| 80 | $C_{11}H_{23}O-$ | H | H | H | H | " | " |
| 81 | $C_{12}H_{25}O-$ | H | H | H | H | " | " |
| 82 | $C_{14}H_{29}O-$ | H | H | H | H | " | " |
| 83 | $C_{16}H_{33}O-$ | H | H | H | H | " | " |
| 84 | $C_2H_5O-$ | H | H | H | H | " | $-COOC^*H(CH_3)C_3H_7$ |
| 85 | $C_4H_9O-$ | H | H | H | H | " | " |
| 86 | $C_8H_{17}O-$ | H | H | H | H | " | " |
| 87 | $C_9H_{19}O-$ | H | H | H | H | " | " |
| 88 | $C_{10}H_{21}O-$ | H | H | H | H | " | " |
| 89 | $C_{11}H_{23}O-$ | H | H | H | H | " | " |
| 90 | $C_{12}H_{25}O-$ | H | H | H | H | " | " |
| 91 | $C_{16}H_{33}O-$ | H | H | H | H | " | " |
| 92 | $C_{10}H_{21}O-$ | H | H | H | H | " | $-COOC^*H(CH_3)C_4H_9$ |
| 93 | $C_{12}H_{25}O-$ | H | H | H | H | " | $-COOC^*H(CH_3)C_5H_{11}$ |
| 94 | $C_{10}H_{21}O-$ | H | H | H | H | " | $-COOC^*H(CH_3)C_7H_{15}$ |
| 95 | $C_8H_{17}O-$ | H | H | H | H | " | $-COOC^*H(CH_3)C_8H_{17}$ |
| 96 | $C_9H_{19}O-$ | H | H | H | H | $-COO-$ | $-COOC^*H(CH_3)C_{10}H_{21}$ |
| 97 | $C_9H_{19}O-$ | H | H | H | H | " | $-COOCH_2C^*H(F)C_3H_7$ |
| 98 | $C_{11}H_{23}O-$ | H | H | H | H | " | $-COOCH_2C^*H(F)C_5H_{11}$ |
| 99 | $C_8H_{17}O-$ | H | H | H | H | " | $-COOCH_2C^*H(F)C_7H_{15}$ |
| 100 | $C_{12}H_{25}O-$ | H | H | H | H | " | $-COOCH_2C^*H(F)C_{10}H_{21}$ |
| 101 | $C_7H_{15}O-$ | H | H | H | H | " | $-COOCH_2C^*H(OCH_3)CH_3$ |
| 102 | $C_{10}H_{21}O-$ | H | H | H | H | " | $-COOCH_2C^*H(OC_3H_7)CH_3$ |
| 103 | $C_5H_{11}-$ | Br | H. | H | H | " | $-COOC^*H(CH_3)C_2H_5$ |
| 104 | $C_8H_{17}-$ | H | H | H | H | " | $-COOC^*H(CH_3)C_6H_{13}$ |
| 105 | $C_4H_9O(CH_2)_4O-$ | H | H | H | H | " | " |
| 106 | $C_6H_{13}C^*H(CH_3)O-$ | H | H | H | H | " | $-COOCH_2C^*H(CH_3)C_2H_5$ |
| 107 | $C_3H_7O-$ | H | H | H | H | " | $-OCH_2C^*H(CH_3)C_2H_5$ |
| 108 | $C_6H_{13}O-$ | H | H | H | H | " | " |
| 109 | $C_8H_{17}O-$ | H | H | H | H | " | " |
| 110 | $C_9H_{19}O-$ | H | H | H | H | " | " |
| 111 | $C_{10}H_{21}O-$ | H | H | H | H | " | " |
| 112 | $C_{11}H_{23}O-$ | H | H | H | H | " | " |
| 113 | $C_{12}H_{25}O-$ | H | H | H | H | " | " |
| 114 | $C_{13}H_{27}O-$ | H | H | H | H | " | " |
| 115 | $C_{14}H_{29}O-$ | H | H | H | H | " | " |
| 116 | $C_{15}H_{31}O-$ | H | H | H | H | " | " |
| 117 | $C_{16}H_{33}O-$ | H | H | H | H | " | " |
| 118 | $C_8H_{17}-$ | H | H | H | H | " | " |
| 119 | $C_8H_{17}O-$ | CN | H | H | H | " | " |
| 120 | $C_{10}H_{21}O-$ | H | H | $C_2H_5$ | H | $-COO-$ | $-OCH_2C^*H(CH_3)C_2H_5$ |
| 121 | $C_{12}H_{25}O-$ | H | H | $OCH_3$ | H | " | " |
| 122 | $C_6H_{13}O-$ | H | H | H | H | " | $-O(CH_2)_3C^*H(CH_3)C_2H_5$ |
| 123 | $C_8H_{17}O-$ | H | H | H | H | " | $-O(CH_2)_3C^*H(CH_3)C_2H_5$ |

TABLE 2-continued

| | | | | | | | |
|---|---|---|---|---|---|---|---|
| 124 | C$_{10}$H$_{21}$O— | H | H | H | H | " | " |
| 125 | C$_{12}$H$_{25}$O— | H | H | H | H | " | " |
| 126 | C$_{14}$H$_{29}$O— | H | H | H | H | " | " |
| 127 | C$_{16}$H$_{33}$O— | H | H | H | H | " | " |
| 128 | C$_8$H$_{17}$— | H | H | H | H | " | " |
| 129 | C$_{10}$H$_{21}$O— | H | H | H | Cl | " | —O(CH$_2$)$_2$C*H(CH$_3$)C$_2$H$_5$ |
| 130 | C$_{12}$H$_{25}$O— | H | H | H | H | " | " |
| 131 | C$_3$H$_7$O— | H | H | H | H | " | —OC*H(CH$_3$)C$_6$H$_{13}$ |
| 132 | C$_7$H$_{15}$O— | H | H | H | H | " | " |
| 133 | C$_8$H$_{17}$O— | H | H | H | H | " | " |
| 134 | C$_9$H$_{19}$O— | H | H | H | H | " | " |
| 135 | C$_{10}$H$_{21}$O— | H | H | H | H | " | " |
| 136 | C$_{11}$H$_{23}$O— | H | H | H | H | " | " |
| 137 | C$_{12}$H$_{25}$O— | H | H | H | H | " | " |
| 138 | C$_{13}$H$_{27}$O— | H | H | H | H | " | " |
| 139 | C$_{14}$H$_{29}$O— | H | H | H | H | " | " |
| 140 | C$_9$H$_{19}$O— | H | H | H | H | " | —OC*H(CH$_3$)C$_2$H$_5$ |
| 141 | C$_{10}$H$_{21}$O— | H | H | H | H | " | " |
| 142 | C$_{12}$H$_{25}$O— | H | H | H | H | " | —OC*H(CH$_3$)C$_3$H$_7$ |
| 143 | C$_8$H$_{17}$O— | H | H | H | H | " | —OCH$_2$C*H(OCH$_3$)CH$_3$ |
| 144 | C$_8$H$_{17}$O— | H | H | H | H | —COO— | —OCH$_2$C*H(OC$_2$H$_5$)CH$_3$ |
| 145 | C$_{12}$H$_{25}$O— | H | H | H | H | " | " |
| 146 | C$_9$H$_{19}$O— | H | H | H | H | " | —OCH$_2$C*H(OC$_3$H$_7$)CH$_3$ |
| 147 | C$_{10}$H$_{21}$O— | H | H | H | H | " | " |
| 148 | C$_{12}$H$_{25}$O— | H | H | H | H | " | —O(CH$_2$)$_2$C*H(OC$_5$H$_{11}$)CH$_3$ |
| 149 | C$_{10}$H$_{21}$O— | H | H | H | H | " | —O(CH$_2$)$_2$C*H(OC$_2$H$_5$)C$_2$H$_5$ |
| 150 | C$_{10}$H$_{21}$O— | H | H | H | H | " | —OCH$_2$C*H(F)C$_5$H$_{11}$ |
| 151 | C$_2$H$_5$C*H(CH$_3$)CH$_2$O— | H | H | H | H | " | —OC$_{10}$H$_{21}$ |
| 152 | C$_6$H$_{13}$C*H(CH$_3$)O— | H | H | H | H | " | —OC$_{10}$H$_{21}$ |
| 153 | C$_2$H$_5$C*H(CH$_3$)(CH$_2$)$_3$O— | H | H | H | H | " | —OC$_{10}$H$_{21}$ |
| 154 | C$_8$H$_{17}$O— | H | H | H | H | " | —OCOC*H(CH$_3$)C$_2$H$_5$ |
| 155 | C$_{12}$H$_{25}$O— | H | H | H | H | " | " |
| 156 | C$_{10}$H$_{21}$O— | H | H | H | H | " | —OCOC*H(OCH$_3$)CH$_3$ |
| 157 | C$_8$H$_{17}$O— | H | H | H | H | " | —COCH$_2$CH$_2$C*H(CH$_3$)C$_2$H$_5$ |
| 158 | H | H | H | H | H | —CH$_2$O— | —COOCH$_2$C*H(CH$_3$)C$_2$H$_5$ |
| 159 | H | H | H | H | H | " | —COO(CH$_2$)$_2$C*H(CH$_2$)$_3$CHCH$_3$<br>CH$_3$      CH$_3$ |
| 160 | C$_8$H$_{17}$O— | H | H | H | H | " | —COO(CH$_2$)$_2$C*H(CH$_2$)$_3$CHCH$_3$<br>CH$_3$      CH$_3$ |
| 161 | H | H | H | H | H | " | —COO(CH$_2$)$_2$C*H(CH$_3$)C$_2$H$_5$ |
| 162 | H | H | H | H | H | " | —COO(CH$_2$)$_3$C*H(CH$_3$)C$_2$H$_5$ |
| 163 | C$_{10}$H$_{21}$O— | H | H | H | H | " | " |
| 164 | H | H | H | H | H | " | —COO(CH$_2$)$_5$C*H(CH$_3$)C$_2$H$_5$ |
| 165 | H | H | H | H | H | " | —COOC*H(CH$_3$)C$_2$H$_5$ |
| 166 | C$_4$H$_9$O— | H | H | H | H | " | " |
| 167 | C$_8$H$_{17}$O— | H | H | H | H | " | " |
| 168 | H | H | H | H | H | —CH$_2$O— | —COOC*H(CH$_3$)C$_3$H$_7$ |
| 169 | C$_6$H$_{13}$O— | H | H | H | H | " | " |
| 170 | H | H | H | H | H | " | —COOC*H(CH$_3$)C$_6$H$_{13}$ |
| 171 | C$_{10}$H$_{21}$O— | H | H | H | H | " | " |
| 172 | C$_8$H$_{17}$O— | H | H | H | H | " | —COOCH$_2$C*H(F)C$_4$H$_9$ |
| 173 | C$_{10}$H$_{21}$O— | H | H | H | H | " | —COOCH$_2$C*H(F)C$_6$H$_{13}$ |
| 174 | C$_9$H$_{19}$O— | H | H | H | H | —OCH$_2$— | —COOCH$_2$C*H(CH$_3$)C$_2$H$_5$ |
| 175 | C$_{10}$H$_{21}$O— | H | H | H | H | " | —COOC*H(CH$_3$)C$_6$H$_{13}$ |
| 176 | C$_2$H$_5$C*H(CH$_3$)CH$_2$O— | H | H | H | H | —OCO— | —OC$_6$H$_{13}$ |
| 177 | " | H | H | H | H | " | —OC$_8$H$_{17}$ |
| 178 | " | H | H | H | H | " | —OC$_{10}$H$_{21}$ |
| 179 | " | H | H | H | H | " | —OC$_{13}$H$_{2}$- |
| 180 | C$_2$H$_5$C*H(CH$_3$)(CH$_2$)$_3$O— | H | H | H | H | " | —OC$_6$H$_{13}$ |
| 181 | " | H | H | H | H | " | —OC$_8$H$_{17}$ |
| 182 | " | H | H | H | H | " | —OC$_{10}$H$_{21}$ |
| 183 | " | H | H | H | H | " | —OC$_{12}$H$_{25}$ |
| 184 | " | H | H | H | H | " | —OC$_{14}$H$_{29}$ |
| 185 | C$_6$H$_{13}$C*H(CH$_3$)O— | H | H | H | H | " | —OC$_8$H$_{17}$ |
| 186 | C$_2$H$_5$C*H(CH$_3$)O— | H | H | H | H | " | —OC$_{10}$H$_{21}$ |
| 187 | C$_2$H$_5$C*H(CH$_3$)CH$_2$— | H | H | H | H | " | —C$_4$H$_9$ |
| 188 | " | H | H | H | H | " | —C$_7$H$_{15}$ |
| 189 | C$_6$H$_{13}$O— | H | H | H | H | " | —OCH$_2$C*H(CH$_3$)C$_2$H$_5$ |
| 190 | C$_8$H$_{17}$O— | H | H | H | H | " | " |
| 191 | C$_{10}$H$_{21}$O— | H | H | H | H | " | " |
| 192 | C$_{12}$H$_{25}$O— | H | H | H | H | " | —OCH$_2$C*H(CH$_3$)C$_2$H$_5$ |
| 193 | C$_6$H$_{13}$O— | H | H | H | H | —OCO— | —O(CH$_2$)$_3$C*H(CH$_3$)C$_2$H$_5$ |
| 194 | C$_8$H$_{17}$O— | H | H | H | H | " | " |
| 195 | C$_{10}$H$_{21}$O— | H | H | H | H | " | " |
| 196 | C$_{12}$H$_{25}$O— | H | H | H | H | " | " |
| 197 | C$_8$H$_{17}$O— | H | H | H | H | " | —OC*H(CH$_3$)C$_6$H$_{13}$ |
| 198 | F— | H | H | H | H | " | " |
| 199 | CN— | H | H | H | H | " | " |

TABLE 2-continued

| No. | R | X1 | X2 | X3 | X4 | Z | R2 |
|---|---|---|---|---|---|---|---|
| 200 | Cl— | H | H | H | H | ″ | ″ |
| 201 | CN— | F | H | H | H | ″ | ″ |
| 202 | $C_2H_5C^*H(CH_3)CH_2OCO-$ | H | H | H | H | ″ | $-OC_8H_{17}$ |
| 203 | ″ | H | H | H | H | ″ | $-OC_{10}H_{21}$ |
| 204 | ″ | H | H | H | H | ″ | $-OC_{12}H_{25}$ |
| 205 | ″ | H | H | H | H | ″ | $-OC_{14}H_{29}$ |
| 206 | $C_3H_7C^*H(CH_3)OCO-$ | H | H | H | H | ″ | $-OC_{10}H_{21}$ |
| 207 | ″ | H | H | H | H | ″ | $-OC_{12}H_{25}$ |
| 208 | $C_2H_5C^*H(CH_3)(CH_2)_3OCO-$ | H | H | H | H | ″ | $-OC_4H_9$ |
| 209 | ″ | H | H | H | H | ″ | $-OC_6H_{13}$ |
| 210 | ″ | H | H | H | H | ″ | $-OC_8H_{17}$ |
| 211 | ″ | H | H | H | H | ″ | $-OC_{10}H_{21}$ |
| 212 | ″ | H | H | H | H | ″ | $-OC_{12}H_{25}$ |
| 213 | ″ | H | H | H | H | ″ | $-OC_{14}H_{29}$ |
| 214 | ″ | H | H | H | H | ″ | $-OC_{16}H_{33}$ |
| 215 | $C_2H_5C^*H(CH_3)OCO-$ | H | H | H | H | ″ | $-OC_{12}H_{25}$ |
| 216 | ″ | H | H | H | H | ″ | $-O(CH_2)_2OC_4H_9$ |
| 217 | $C_4H_9C^*H(CH_3)OCO-$ | H | H | H | H | ″ | $-OC_8H_{17}$ |
| 218 | $C_4H_9C^*H(CH_3)OCO-$ | H | H | H | H | $-OCO-$ | $-OC_9H_{19}$ |
| 219 | ″ | H | H | H | H | ″ | $-OC_{10}H_{21}$ |
| 220 | $C_5H_{11}C^*H(CH_3)OCO-$ | H | H | H | H | ″ | $-OC_7H_{15}$ |
| 221 | ″ | H | H | H | H | ″ | $-OC_9H_{19}$ |
| 222 | ″ | H | H | H | H | ″ | $-OC_{11}H_{23}$ |
| 223 | $CH_3C^*H(OC_2H_5)CH_2O-$ | H | H | H | H | ″ | $-OC_8H_{17}$ |
| 224 | $CH_3C^*H(OC_4H_9)CH_2O-$ | H | H | H | H | ″ | $-OC_{10}H_{21}$ |
| 225 | $C_2H_5C^*H(F)CH_2OCO-$ | H | H | H | H | ″ | $-OC_7H_{15}$ |
| 226 | $C_4H_9C^*H(F)CH_2OCO-$ | H | H | H | H | ″ | $-OC_{10}H_{21}$ |
| 227 | $C_{10}H_{21}O-$ | H | H | H | H | $-CH_2CH_2-$ | $-OCH_2C^*H(CH_3)C_2H_5$ |
| 228 | $C_9H_{19}O-$ | H | H | H | H | $-CH=N-$ | $-(CH_2)_3C^*H(CH_3)C_2H_5$ |
| 229 | $C_7H_{15}O-$ | F | H | H | H | $-CH=CH-$ | $-OC^*H(CH_3)C_6H_{13}$ |
| 230 | $C_{11}H_{23}O-$ | H | H | H | H | $-C\equiv C-$ | $-CH_2C^*H(CH_3)C_2H_5$ |

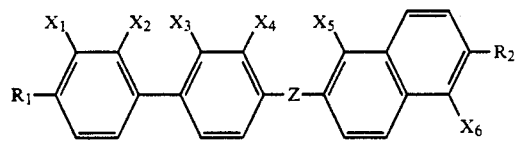

| Example Compound No. | R1 | X1 | X2 | X3 | X4 | X5 | X6 | Z | R2 |
|---|---|---|---|---|---|---|---|---|---|
| 231 | $CH_3O-$ | H | H | H | H | H | H | $-COO-$ | $-COOCH_2C^*H(CH_3)C_2H_5$ |
| 232 | $C_8H_{17}O-$ | H | H | H | H | H | H | ″ | ″ |
| 233 | $C_8H_{17}O-$ | H | H | H | H | Cl | H | ″ | ″ |
| 234 | $C_{12}H_{25}O-$ | H | F | H | H | H | H | ″ | ″ |
| 235 | $C_7H_{15}O-$ | H | H | H | H | H | H | ″ | $-COOC^*H(CH_3)C_2H_5$ |
| 236 | $C_8H_{17}O-$ | H | H | H | H | H | H | ″ | ″ |
| 237 | $C_{13}H_{27}O-$ | Cl | H | H | H | H | H | ″ | ″ |
| 238 | $C_7H_{15}-$ | H | H | H | H | H | H | ″ | ″ |
| 239 | $C_8H_{17}-$ | H | H | H | H | H | H | ″ | ″ |
| 240 | $C_{12}H_{25}-$ | H | H | H | H | H | H | ″ | ″ |
| 241 | $C_7H_{15}O-$ | H | H | H | H | H | H | ″ | $-COOC^*H(CH_3)C_3H_7$ |
| 242 | $C_{10}H_{21}O-$ | H | H | H | H | H | H | ″ | $-COOC^*H(CH_3)C_4H_9$ |
| 243 | $C_4H_9O-$ | H | H | H | H | H | H | ″ | $-COOC^*H(CH_3)C_6H_{13}$ |
| 244 | $C_7H_{15}O-$ | H | H | H | H | H | H | ″ | ″ |
| 245 | $C_8H_{17}O-$ | H | H | H | H | H | H | ″ | ″ |
| 246 | $C_{10}H_{21}O-$ | H | H | H | H | H | H | ″ | ″ |
| 247 | $C_{12}H_{25}O-$ | H | H | H | H | H | H | ″ | ″ |
| 248 | $C_7H_{15}-$ | H | H | H | H | H | H | ″ | ″ |
| 249 | $C_8H_{17}-$ | H | H | H | H | H | H | ″ | ″ |
| 250 | $C_{10}H_{21}-$ | H | H | H | H | H | H | ″ | ″ |
| 251 | $C_7H_{15}O-$ | Cl | H | H | H | H | H | ″ | ″ |
| 252 | $C_9H_{19}O-$ | Cl | H | H | H | H | H | ″ | ″ |
| 253 | $C_{10}H_{21}O-$ | F | H | H | H | H | H | ″ | ″ |
| 254 | $C_{12}H_{25}O-$ | F | H | H | H | H | H | $-COO-$ | $-COOC^*H(CH_3)C_6H_{13}$ |
| 255 | $C_{12}H_{25}O-$ | H | H | H | F | H | H | ″ | ″ |
| 256 | $C_8H_{17}O-$ | H | H | H | H | H | H | ″ | $-COOC^*H(CH_3)C_8H_{17}$ |
| 257 | $C_7H_{15}-$ | H | H | H | H | H | H | ″ | ″ |
| 258 | $C_{12}H_{25}O-$ | H | H | H | H | H | H | ″ | $-COOC^*H(CH_3)C_{10}H_{21}$ |
| 259 | $C_{10}H_{21}O-$ | H | H | H | H | H | H | ″ | $-COO(CH_2)_3C^*H(CH_3)C_2H_5$ |
| 260 | $C_7H_{15}O-$ | H | H | H | H | H | H | ″ | $-COOCH_2C^*H(OCH_3)CH_3$ |
| 261 | $C_9H_{19}O-$ | H | H | H | H | H | H | ″ | $-COOCH_2C^*H(OC_3H_7)CH_3$ |
| 262 | $C_9H_{19}O-$ | H | H | H | H | H | H | ″ | $-COO(CH_2)_2C^*H(OC_4H_9)C_2H_5$ |
| 263 | $C_8H_{17}O-$ | H | H | H | H | H | H | ″ | $-COOCH_2C^*H(F)CH_3$ |
| 264 | $C_{10}H_{21}O-$ | H | H | H | H | H | H | ″ | $-COOCH_2C^*H(F)C_6H_{13}$ |
| 265 | $C_{12}H_{25}O-$ | H | H | H | H | H | H | ″ | $-COOCH_2C^*H(F)C_9H_{19}$ |
| 266 | $C_4H_9O-$ | H | H | H | H | H | H | ″ | $-OCH_2C^*H(CH_3)C_2H_5$ |
| 267 | $C_8H_{17}O-$ | H | H | H | H | H | H | ″ | ″ |
| 268 | $C_{12}H_{25}O-$ | H | H | H | H | H | H | ″ | ″ |
| 269 | $C_2H_5C^*H(CH_3)CH_2O-$ | H | H | H | H | H | H | ″ | $-OC_{10}H_{21}$ |

TABLE 2-continued

| | | | | | | | | | |
|---|---|---|---|---|---|---|---|---|---|
| 270 | $C_{10}H_{21}O-$ | H | H | H | H | H | H | " | $-OC^*H(CH_3)C_2H_5$ |
| 271 | $C_5H_{11}O-$ | H | H | H | H | H | H | " | $-OC^*H(CH_3)C_6H_{13}$ |
| 272 | $C_7H_{15}O-$ | H | H | H | H | H | H | " | " |
| 273 | $C_8H_{17}O-$ | H | H | H | H | H | H | " | " |
| 274 | $C_{12}H_{25}O-$ | H | H | H | H | H | H | " | " |
| 275 | $C_9H_{19}O-$ | H | H | H | H | H | H | " | $-OC^*H(CH_3)C_3H_7$ |
| 276 | $C_6H_{13}O-$ | H | H | H | H | H | H | " | $-O(CH_2)_2C^*H(CH_2)_3CHCH_3$ <br> $\qquad CH_3 \qquad CH_3$ |
| 277 | $C_{10}H_{21}O-$ | H | H | H | H | H | H | " | |
| 278 | $C_8H_{17}O-$ | H | H | H | H | H | H | $-COO-$ | $-O(CH_2)_5C^*H(CH_3)C_2H_5$ |
| 279 | $C_{12}H_{25}O-$ | H | H | H | H | H | H | " | $-OCH_2C^*H(CH_3)C_4H_9$ |
| 280 | $C_7H_{15}O-$ | H | H | H | H | H | H | " | $-OCH_2C^*H(OC_2H_5)CH_3$ |
| 281 | $C_{10}H_{21}O-$ | H | H | H | H | H | H | " | $-O(CH_2)_2C^*H(OC_3H_7)C_2H_5$ |
| 282 | $C_{12}H_{25}O-$ | H | H | H | H | H | H | " | $-OCH_2C^*H(F)C_6H_{13}$ |
| 283 | $C_6H_{13}C^*H(CH_3)O-$ | H | H | H | H | H | H | " | $-C_4H_9$ |
| 284 | " | H | H | H | H | H | H | " | $-C_6H_{13}$ |
| 285 | " | H | H | H | H | H | H | " | $-C_7H_{15}$ |
| 286 | " | H | H | H | H | H | H | " | $-OC_6H_{13}$ |
| 287 | $C_{18}H_{17}O-$ | H | H | H | H | H | H | " | $-OCOC^*H(CH_3)C_3H_7$ |
| 288 | $C_8H_{17}-$ | H | H | H | H | H | H | " | " |
| 289 | $C_{10}H_{21}O-$ | H | H | H | H | H | H | " | $-OCOCH_2C^*H(CH_3)C_2H_5$ |
| 290 | $C_2H_5C^*H(CH_3)CH_2OCO-$ | H | H | H | H | H | H | $-OCO-$ | $-OC_6H_{13}$ |
| 291 | $C_2H_5C^*H(CH_3)CH_2OCO-$ | H | H | H | H | H | H | " | $-OC_8H_{17}$ |
| 292 | $C_6H_{13}C^*H(CH_3)OCO-$ | H | H | H | H | H | Cl | " | $-OC_{10}H_{21}$ |
| 293 | $C_6H_{13}C^*H(CH_3)OCO-$ | H | H | H | H | H | H | " | $-C_8H_{17}$ |
| 294 | $C_2H_5C^*H(CH_3)OCO-$ | H | H | F | H | H | H | " | $-OC_8H_{17}$ |
| 295 | " | H | H | H | F | H | H | " | $-OC_{10}H_{21}$ |
| 296 | $C_7H_{15}O-$ | H | H | H | H | H | H | $-CH_2O-$ | $-COOC^*H(CH_3)C_6H_{13}$ |
| 297 | $C_8H_{17}O-$ | H | H | H | H | H | H | $-OCH_2-$ | " |
| 298 | $C_8H_{17}O-$ | H | H | H | H | H | H | $-CH_2O-$ | $-COOC^*H(CH_3)C_2H_5$ |
| 299 | $C_{10}H_{21}O-$ | H | H | H | H | H | H | $-OCH_2-$ | " |
| 300 | $C_8H_{17}-$ | H | H | H | H | H | H | $-CH_2O-$ | $-COOCH_2C^*H(CH_3)C_2H_5$ |
| 301 | $C_{10}H_{21}-$ | H | H | H | H | H | H | $-OCH_2-$ | " |

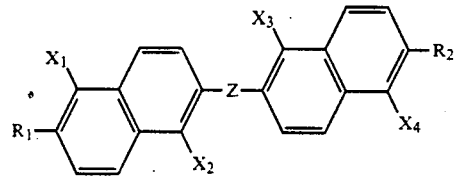

| Example Compound No. | $R_1$ | $X_1$ | $X_2$ | $X_3$ | $X_4$ | Z | $R_2$ |
|---|---|---|---|---|---|---|---|
| 302 | $C_3H_7O-$ | H | H | H | H | $-COO-$ | $-COOCH_2C^*H(CH_3)C_2H_5$ |
| 303 | $C_6H_{13}O-$ | H | H | H | H | " | " |
| 304 | $C_8H_{17}O-$ | H | H | H | H | " | " |
| 305 | $C_{10}H_{21}O-$ | H | H | H | H | " | " |
| 306 | $C_{12}H_{25}O-$ | H | H | H | H | " | " |
| 307 | $C_{14}H_{29}O-$ | H | H | H | H | " | " |
| 308 | $C_{16}H_{33}O-$ | H | H | H | H | " | " |
| 309 | $C_9H_{19}O-$ | H | H | H | H | " | $-COOC^*H(CH_3)C_2H_5$ |
| 310 | $C_{11}H_{23}O-$ | H | H | H | H | " | $-COOC^*H(CH_3)C_6H_{13}$ |
| 311 | $C_{10}H_{21}O-$ | Cl | H | H | H | " | $-COOC^*H(CH_3)C_3H_7$ |
| 312 | $C_8H_{17}-$ | H | H | H | Cl | " | " |
| 313 | $C_9H_{19}-$ | H | H | H | H | " | $-COOCH_2C^*H(OC_3H_7)CH_3$ |
| 314 | $C_{11}H_{23}-$ | H | H | H | H | " | $-COOCH_2C^*H(F)C_6H_{13}$ |
| 315 | $C_8H_{17}O-$ | H | H | H | H | " | $-OCH_2C^*H(CH_3)C_2H_5$ |
| 316 | $C_{10}H_{21}O-$ | H | H | H | H | " | $-OC^*H(CH_3)C_2H_5$ |
| 317 | $C_{10}H_{21}-$ | H | H | H | H | " | $-OC^*H(CH_3)C_6H_{13}$ |
| 318 | $C_2H_5C^*H(CH_3)CH_2O-$ | H | H | H | H | " | $-OC_{10}H_{21}$ |
| 319 | $C_2H_5C^*H(CH_3)(CH_2)_3O-$ | H | H | H | H | " | " |
| 320 | $C_8H_{17}O-$ | H | H | H | H | " | $-OCH_2C^*H(OC_2H_5)CH_3$ |
| 321 | $C_{10}H_{21}O-$ | H | H | H | H | " | $-OCH_2C^*H(OC_5H_{11})CH_3$ |
| 322 | $C_7H_{15}O-$ | H | H | H | H | " | $-OCH_2C^*H(F)C_5H_{11}$ |
| 323 | $C_9H_{19}O-$ | H | H | H | H | " | $-OCH_2C^*H(F)C_7H_{15}$ |
| 324 | $C_6H_{13}O-$ | H | H | H | H | " | $-CH_2C^*H(CH_3)C_2H_5$ |
| 325 | $C_8H_{17}-$ | H | H | H | H | $-COO-$ | $-CH_2C^*H(CH_3)C_2H_5$ |
| 326 | $C_6H_{13}C^*H(CH_3)O-$ | H | H | H | H | " | $-C_6H_{13}$ |
| 327 | " | H | H | H | H | " | $-C_8H_{17}$ |
| 328 | " | H | H | H | H | " | $-CH_2C^*H(CH_3)C_2H_5$ |
| 329 | $C_6H_{13}O-$ | H | H | H | H | " | $-OCOC^*H(CH_3)C_2H_5$ |
| 330 | $C_7H_{15}-$ | H | H | H | H | " | " |
| 331 | $C_{10}H_{21}O-$ | H | H | H | H | " | $-OCO(CH_2)_2C^*H(CH_3)C_2H_5$ |
| 332 | $C_8H_{17}-$ | H | H | H | H | $-CH_2O-$ | $-COOCH_2C^*H(CH_3)C_2H_5$ |
| 333 | $C_{10}H_{21}O-$ | H | H | H | H | " | " |
| 334 | $C_{12}H_{25}O-$ | H | H | H | H | " | $-COOC^*H(CH_3)C_2H_5$ |

TABLE 2-continued

| | | | | | | | |
|---|---|---|---|---|---|---|---|
| 335 | C$_{10}$H$_{21}$O— | H | H | H | H | " | —COOC*H(CH$_3$)C$_6$H$_{13}$ |
| 336 | C$_6$H$_{13}$C*H(CH$_3$)O— | H | H | H | H | " | —COOCH$_2$C*H(CH$_3$)C$_2$H$_5$ |

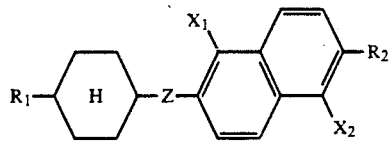

| Example Compound No. | R$_1$ | X$_1$ | X$_2$ | Z | R$_2$ |
|---|---|---|---|---|---|
| 337 | CH$_3$— | H | H | —COO— | —COOCH$_2$C*H(CH$_3$)C$_2$H$_5$ |
| 338 | C$_5$H$_{11}$— | H | H | " | " |
| 339 | C$_{10}$H$_{21}$— | H | H | " | " |
| 340 | C$_4$H$_9$— | H | H | " | —COOC*H(CH$_3$)C$_6$H$_{13}$ |
| 341 | C$_9$H$_{19}$— | H | H | " | " |
| 342 | C$_7$H$_{15}$— | H | H | " | —COO(CH$_2$)$_3$C*H(CH$_3$)C$_2$H$_5$ |
| 343 | C$_8$H$_{17}$— | H | H | " | " |
| 344 | C$_5$H$_{11}$— | H | H | " | —COO(CH$_2$)$_2$C*H(CH$_2$)$_3$CHCH$_3$<br>                          CH$_3$       CH$_3$ |
| 345 | C$_5$H$_{11}$— | H | H | " | —COOC*H(CH$_3$)C$_3$H$_7$ |
| 346 | C$_5$H$_{11}$— | Cl | H | " | —COOC*H(CH$_3$)C$_2$H$_5$ |
| 347 | C$_5$H$_{11}$— | H | H | " | —COOCH$_2$C*H(F)C$_6$H$_{13}$ |
| 348 | C$_5$H$_{11}$— | H | H | " | —COOCH$_2$C*H(OC$_2$H$_5$)CH$_3$ |
| 349 | C$_5$H$_{11}$— | H | H | " | —OCH$_2$C*H(CH$_3$)C$_2$H$_5$ |
| 350 | C$_7$H$_{15}$— | H | Cl | " | " |
| 351 | C$_3$H$_7$— | H | H | " | —OC*H(CH$_3$)C$_6$H$_{13}$ |
| 352 | C$_9$H$_{19}$— | H | H | " | " |
| 353 | C$_5$H$_{11}$— | H | H | " | —OC*H(CH$_3$)C$_2$H$_5$ |
| 354 | C$_{10}$H$_{21}$— | H | H | " | —OC*H(CH$_3$)C$_4$H$_9$ |
| 355 | C$_5$H$_{11}$— | H | H | " | —COOCH$_2$C*H(OCH$_3$)CH$_3$ |
| 356 | C$_8$H$_{17}$— | H | H | " | —COOCH$_2$C*H(OC$_4$H$_9$)CH$_3$ |
| 357 | C$_4$H$_9$— | H | H | " | —COOCH$_2$C*H(F)C$_4$H$_9$ |
| 358 | C$_9$H$_{19}$— | H | H | " | —COOCH$_2$C*H(F)C$_8$H$_{17}$ |
| 359 | C$_5$H$_{11}$— | H | H | " | —OCOC*H(CH$_3$)C$_2$H$_5$ |
| 360 | C$_2$H$_5$C*H(CH$_3$)CH$_2$— | H | H | —COO— | —C$_6$H$_{13}$ |
| 361 | " | H | H | " | —OC$_5$H$_{11}$ |
| 362 | " | H | H | " | —OC*H(CH$_3$)C$_6$H$_{13}$ |
| 363 | C$_5$H$_{11}$— | H | H | single bond | —CH$_2$C*H(CH$_3$)C$_2$H$_5$ |
| 364 | C$_8$H$_{17}$— | H | H | " | —OC*H(CH$_3$)C$_6$H$_{13}$ |
| 365 | CH$_3$— | H | H | —OCO— | —CH$_2$C*H(CH$_3$)C$_2$H$_5$ |
| 366 | C$_7$H$_{15}$— | H | H | " | —OCH$_2$C*H(CH$_3$)C$_2$H$_5$ |
| 367 | C$_8$H$_{17}$— | H | H | —OCO— | —OC*H(CH$_3$)C$_6$H$_{13}$ |
| 368 | C$_5$H$_{11}$— | H | H | " | —COOCH$_2$C*H(CH$_3$)C$_2$H$_5$ |
| 369 | C$_7$H$_{15}$— | H | H | " | —COOC*H(CH$_3$)C$_6$H$_{13}$ |
| 370 | C$_5$H$_7$— | H | H | —CH$_2$O— | " |
| 371 | C$_7$H$_{15}$— | H | H | " | —COOC*H(CH$_3$)C$_2$H$_5$ |
| 372 | C$_8$H$_{17}$— | H | H | " | —OCH$_2$C*H(CH$_3$)C$_2$H$_5$ |
| 373 | C$_{10}$H$_{21}$— | H | H | " | —CH$_2$C*H(CH$_3$)C$_2$H$_5$ |
| 374 | C$_2$H$_5$C*H(CH$_3$)CH$_2$— | H | H | " | —C$_6$H$_{13}$ |
| 375 | " | H | H | " | —OC$_8$H$_{17}$ |
| 376 | C$_4$H$_9$— | H | H | —OCH$_2$— | —OC*H(CH$_3$)C$_2$H$_5$ |
| 377 | C$_8$H$_{17}$— | H | H | " | —OC*H(CH$_3$)C$_6$H$_{13}$ |

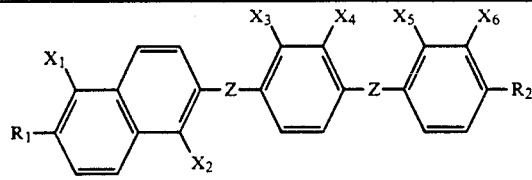

| Example Compound No. | R$_1$ | X$_1$ | X$_2$ | X$_3$ | X$_4$ | X$_5$ | X$_6$ | Z | R$_2$ |
|---|---|---|---|---|---|---|---|---|---|
| 378 | C$_4$H$_9$O— | H | H | Cl | H | H | H | —COO— | —OCH$_2$C*H(CH$_3$)C$_2$H$_5$ |
| 379 | C$_8$H$_{17}$O— | H | H | Cl | H | H | H | " | " |
| 380 | C$_{10}$H$_{21}$O— | H | H | Cl | H | H | H | " | " |
| 381 | C$_{12}$H$_{25}$O— | H | H | Cl | H | H | H | " | " |
| 382 | C$_{13}$H$_{27}$O— | H | H | H | H | H | H | " | " |
| 383 | C$_7$H$_{15}$O— | H | H | F | H | H | H | " | " |
| 384 | C$_9$H$_{19}$O— | H | H | H | H | H | Cl | " | " |
| 385 | C$_{10}$H$_{21}$O— | H | H | H | H | F | H | " | " |
| 386 | C$_8$H$_{17}$O— | Cl | H | H | H | H | H | " | " |
| 387 | C$_{14}$H$_{29}$O— | H | H | Cl | H | H | H | " | " |
| 388 | C$_{16}$H$_{33}$O— | H | H | Cl | H | H | H | " | " |

TABLE 2-continued

| | | | | | | | | | |
|---|---|---|---|---|---|---|---|---|---|
| 389 | C$_8$H$_{17}$O— | H | H | H | H | H | H | " | —COOCH$_2$C*H(CH$_3$)C$_2$H$_5$ |
| 390 | C$_8$H$_{17}$— | H | H | H | H | H | H | " | " |
| 391 | C$_{10}$H$_{21}$O— | H | H | H | H | H | Cl | " | " |
| 392 | C$_{10}$H$_{21}$O— | H | H | H | H | H | F | " | " |
| 393 | C$_{12}$H$_{25}$O— | H | H | H | F | H | H | " | " |
| 394 | C$_{10}$H$_{21}$O— | H | H | H | H | H | H | " | —COOC*H(CH$_3$)C$_2$H$_5$ |
| 395 | C$_{13}$H$_{27}$O— | H | H | H | H | H | H | " | —COOC*H(CH$_3$)C$_6$H$_{13}$ |
| 396 | C$_{10}$H$_{21}$— | H | H | Cl | H | H | H | " | —CH$_2$C*H(CH$_3$)C$_2$H$_5$ |
| 397 | C$_2$H$_5$C*H(CH$_3$)CH$_2$OCO— | H | H | Cl | H | H | H | —OCO— | —OC$_8$H$_{17}$ |
| 398 | " | H | H | H | F | H | H | " | —C$_{10}$H$_{21}$ |
| 399 | C$_6$H$_{13}$C*H(CH$_3$)OCO— | H | Cl | H | H | H | H | " | —OC$_{10}$H$_{21}$ |
| 400 | C$_6$H$_{13}$O— | H | H | H | H | H | H | " | —OC*H(CH$_3$)C$_6$H$_{13}$ |
| 401 | C$_{10}$H$_{21}$O— | H | H | H | H | H | H | " | " |

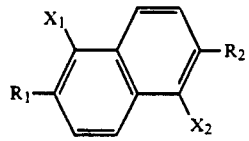

| Example Compound No. | R$_1$ | X$_1$ | X$_2$ | R$_2$ |
|---|---|---|---|---|
| 402 | C$_3$H$_7$O— | H | H | —COOCH$_2$C*H(CH$_3$)C$_2$H$_5$ |
| 403 | C$_6$H$_{13}$O— | H | H | " |
| 404 | C$_8$H$_{17}$O— | H | H | " |
| 405 | C$_9$H$_{19}$O— | H | H | " |
| 406 | C$_{10}$H$_{21}$O— | H | H | " |
| 407 | C$_{11}$H$_{23}$O— | H | H | " |
| 408 | C$_{12}$H$_{25}$O— | H | H | " |
| 409 | C$_{14}$H$_{29}$O— | H | H | " |
| 410 | C$_{16}$H$_{33}$O— | H | H | " |
| 411 | C$_{18}$H$_{37}$O— | H | H | " |
| 412 | C$_8$H$_{17}$— | H | H | " |
| 413 | C$_6$H$_{13}$O— | H | H | —COOC*H(CH$_3$)C$_2$H$_5$ |
| 414 | C$_8$H$_{17}$O— | H | H | " |
| 415 | C$_9$H$_{19}$O— | Cl | H | " |
| 416 | C$_{10}$H$_{21}$O— | H | H | " |
| 417 | C$_{11}$H$_{23}$O— | H | H | " |
| 418 | C$_{12}$H$_{25}$O— | H | H | " |
| 419 | C$_{14}$H$_{29}$O— | H | H | " |
| 420 | C$_{16}$H$_{33}$O— | H | H | " |
| 421 | C$_{18}$H$_{37}$O— | H | H | " |
| 422 | C$_6$H$_{13}$— | H | H | " |
| 423 | C$_8$H$_{17}$— | H | H | " |
| 424 | C$_6$H$_{13}$O— | H | H | —COOC*H(CH$_3$)C$_3$H$_7$ |
| 425 | C$_8$H$_{17}$O— | H | H | " |
| 426 | C$_{10}$H$_{21}$O— | H | H | " |
| 427 | C$_{14}$H$_{29}$O— | H | H | " |
| 428 | C$_{16}$H$_{33}$O— | H | H | " |
| 429 | C$_{18}$H$_{37}$O— | H | H | " |
| 430 | C$_8$H$_{17}$— | H | H | " |
| 431 | C$_{10}$H$_{21}$— | H | H | " |
| 432 | C$_6$H$_{13}$O— | H | H | —COOC*H(CH$_3$)C$_4$H$_9$ |
| 433 | C$_8$H$_{17}$O— | H | H | " |
| 434 | C$_{10}$H$_{21}$O— | H | H | " |
| 435 | C$_{12}$H$_{25}$O— | H | H | " |
| 436 | C$_{16}$H$_{33}$O— | H | H | " |
| 437 | C$_8$H$_{17}$— | H | H | " |
| 438 | C$_{10}$H$_{21}$— | H | H | " |
| 439 | C$_8$H$_{17}$O— | H | H | —COOC*H(CH$_3$)C$_6$H$_{13}$ |
| 440 | C$_7$H$_{15}$O— | H | H | —COO(CH$_2$)$_2$C*H(CH$_3$)C$_2$H$_5$ |
| 441 | C$_{10}$H$_{21}$O— | H | H | —COO(CH$_2$)$_2$C*H(CH$_2$)$_3$CH=CCH$_3$<br>   CH$_3$            CH$_3$ |
| 442 | C$_{10}$H$_{21}$O— | H | H | —COOC*H(CH$_3$)C$_9$H$_{19}$ |
| 443 | C$_6$H$_{13}$O— | H | H | —COOCH$_2$C*H(OCH$_3$)CH$_3$ |
| 444 | C$_{10}$H$_{21}$— | H | H | —COOCH$_2$C*H(OC$_2$H$_5$)CH$_3$ |
| 445 | C$_8$H$_{17}$O— | H | H | —COOCH$_2$C*H(OC$_3$H$_7$)CH$_3$ |
| 446 | C$_8$H$_{17}$O— | H | H | —COO(CH$_2$)$_2$C*H(OC$_2$H$_5$)CH$_3$ |
| 447 | C$_8$H$_{17}$O— | H | H | —COOC*H(CN)C$_2$H$_5$ |
| 448 | C$_8$H$_{17}$O— | H | H | —COOCH$_2$C*H(CH$_3$)CO$_2$CH$_3$ |
| 449 | C$_{11}$H$_{23}$O— | H | H | —COOCH$_2$C*H(CH$_3$)CO$_2$C$_2$H$_5$ |
| 450 | C$_{10}$H$_{21}$O— | H | H | —COOC*H(CH$_3$)CH$_2$CO$_2$C$_2$H$_5$ |
| 451 | C$_{10}$H$_{21}$O— | H | H | —COOC*H(CH$_3$)CH$_2$CO$_2$C$_4$H$_9$ |
| 452 | C$_8$H$_{17}$O— | H | H | —OCOC*H(CH$_3$)C$_2$H$_5$ |
| 453 | C$_{10}$H$_{21}$O— | H | H | " |
| 454 | C$_8$H$_{17}$O— | H | Cl | " |
| 455 | C$_8$H$_{17}$O— | H | H | —OCOC*H(CH$_3$)C$_3$H$_7$ |

TABLE 2-continued

| No. | R₁ | X₁ | X₂ | R₂ |
|---|---|---|---|---|
| 456 | $C_8H_{17}O-$ | H | H | $-OCO(CH_2)_2C^*H(CH_3)C_2H_5$ |
| 457 | $C_{10}H_{21}O-$ | H | H | " |
| 458 | $C_{12}H_{25}O-$ | H | H | " |
| 459 | $C_{14}H_{29}O-$ | H | H | " |
| 460 | $C_{10}H_{21}O-$ | H | H | $-OCOCH_2C^*H(CH_2)_3CHCH_3$ <br>                         $CH_3$     $CH_3$ |
| 461 | $C_8H_{17}O-$ | H | H | $-OCOC^*H(Cl)C^*H(CH_3)C_2H_5$ |
| 462 | $C_{10}H_{21}O-$ | H | H | " |
| 463 | $C_{10}H_{21}O-$ | H | H | $-OCOC^*H(Br)C^*H(CH_3)C_2H_5$ |
| 464 | $C_{12}H_{25}O-$ | H | H | " |
| 465 | $C_{10}H_{21}O-$ | H | H | $-OCOC^*H(Br)CH(CH_3)CH_3$ |
| 466 | $C_2H_5C^*H(CH_3)CH_2OCO-$ | H | H | $-COOCH_2C^*H(CH_3)C_2H_5$ |
| 467 | $C_6H_{13}C^*H(CH_3)OCO-$ | H | H | $-COOC^*H(CH_3)C_6H_{13}$ |
| 468 | $C_2H_5C^*H(CH_3)OCO-$ | H | H | " |
| 469 | $C_6H_{13}C^*H(CH_3)O-$ | H | H | $-OC^*H(CH_3)C_6H_{13}$ |
| 470 | $C_6H_{13}C^*H(CH_3)O-$ | H | H | $-CH_2C^*H(CH_3)C_2H_5$ |
| 471 | $C_2H_5C^*H(CH_3)O-$ | H | H | $-CN$ |
| 472 | $C_6H_{13}C^*H(CH_3)O-$ | H | H | $-Br$ |
| 473 | $C_6H_{13}C^*H(CH_3)O-$ | H | H | $-COOC_4H_9$ |
| 474 | $C_6H_{13}C^*H(CH_3)O-$ | H | H | $-COOCH_2C^*H(CH_3)C_2H_5$ |

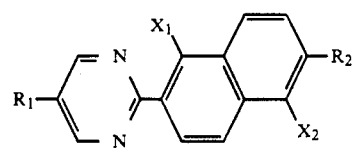

| Example Compound No. | R₁ | X₁ | X₂ | R₂ |
|---|---|---|---|---|
| 475 | $C_8H_{17}O-$ | H | H | $-OCH_2C^*H(CH_3)C_4H_9$ |
| 476 | $C_{10}H_{21}O-$ | H | H | $-OCH_2C^*H(OCH_3)CH_3$ |
| 477 | $C_{12}H_{25}O-$ | H | H | $-OCH_2C^*H(OC_3H_7)CH_3$ |
| 478 | $C_9H_{19}-$ | H | H | $-(CH_2)_3C^*H(CH_3)C_2H_5$ |
| 479 | $C_{11}H_{23}-$ | H | H | $-OCOC^*H(CH_3)C_2H_5$ |
| 480 | $C_2H_5C^*H(CH_3)(CH_2)_5-$ | H | H | $-OC_8H_{17}$ |
| 481 | $C_9H_{19}-$ | H | H | $-COOC^*H(CH_3)C_6H_{13}$ |

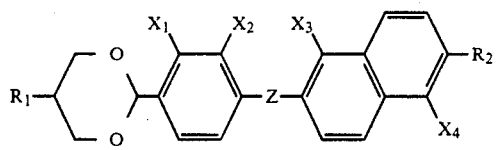

| Example Compound No. | R₁ | X₁ | X₂ | X₃ | X₄ | Z | R₂ |
|---|---|---|---|---|---|---|---|
| 482 | $C_8H_{17}-$ | H | H | H | H | $-COO-$ | $-COOC^*H(CH_3)C_6H_{13}$ |
| 483 | $C_9H_{19}-$ | H | H | H | H | " | $-OCH_2C^*H(CH_3)C_2H_5$ |
| 484 | $C_{11}H_{23}-$ | H | H | Cl | H | " | $-OC^*H(CH_3)C_3H_7$ |
| 485 | $C_{12}H_{25}-$ | H | H | H | H | " | $-OCH_2C^*H(OC_2H_5)CH_3$ |
| 486 | $C_9H_{19}-$ | H | H | H | H | $-N=CH-$ | $-OC^*H(CH_3)C_2H_5$ |
| 487 | $C_{14}H_{29}-$ | H | H | H | H | $-N=N-$ | $-(CH_2)_2C^*H(CH_3)C_2H_5$ |

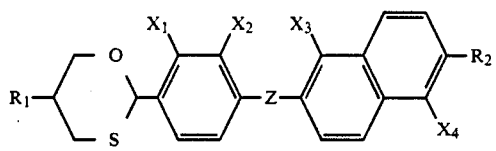

| Example Compound No. | R₁ | X₁ | X₂ | X₃ | X₄ | Z | R₂ |
|---|---|---|---|---|---|---|---|
| 488 | $C_5H_{11}-$ | H | H | H | H | $-COO-$ | $-COOC^*H(CH_3)C_5H_{11}$ |
| 489 | $C_{10}H_{21}-$ | H | H | H | H | " | $-COO(CH_2)_4C^*H(CH_3)C_2H_5$ |
| 490 | $C_8H_{17}-$ | H | H | H | H | " | $-OC^*H(CH_3)C_2H_5$ |
| 491 | $C_{11}H_{23}-$ | H | H | H | H | " | $-OCOCH_2C^*H(CH_3)C_2H_5$ |
| 492 | $C_7H_{15}-$ | H | H | H | H | $-CH=N-$ | $-(CH_2)_2C^*H(CH_3)C_2H_5$ |

TABLE 2-continued

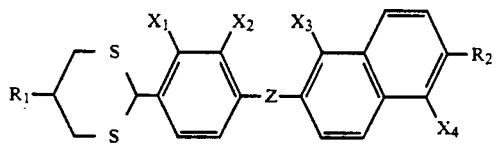

| Example Compound No. | R₁ | X₁ | X₂ | X₃ | X₄ | Z | R₂ |
|---|---|---|---|---|---|---|---|
| 493 | $C_3H_7-$ | H | H | H | H | $-COO-$ | $-COO(CH_2)_3C^*H(CH_3)C_2H_5$ |
| 494 | $C_{10}H_{21}-$ | H | H | Cl | H | " | $-COOC^*H(CH_3)C_6H_{13}$ |
| 495 | $C_5H_{11}-$ | H | H | H | H | $-N=N-$ | $-OCH_2C^*H(CH_3)C_2H_5$ |
| 496 | $C_7H_{15}-$ | H | H | H | H | $-N(O)=N-$ | $-OC^*H(CH_3)C_7H_{15}$ |

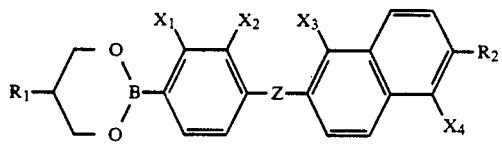

| Example Compound No. | R₁ | X₁ | X₂ | X₃ | X₄ | Z | R₂ |
|---|---|---|---|---|---|---|---|
| 497 | $C_7H_{15}-$ | H | H | H | H | $-COO-$ | $-COOCH_2C^*H(CH_3)C_2H_5$ |
| 498 | $C_{10}H_{21}-$ | H | H | Cl | H | " | $-COO(CH_2)_2C^*H(CH_3)C_2H_5$ |
| 499 | $C_{12}H_{25}-$ | H | H | H | H | " | $-COOC^*H(CH_3)C_6H_{13}$ |
| 500 | $C_8H_{17}-$ | H | H | H | H | " | $-OC^*H(CH_3)C_2H_5$ |
| 501 | $C_{10}H_{21}-$ | H | H | H | H | " | $-OCOCH_2C^*H(CH_3)C_2H_5$ |
| 502 | $C_{11}H_{23}-$ | H | F | H | H | " | $-CH_2C^*H(CH_3)C_2H_5$ |

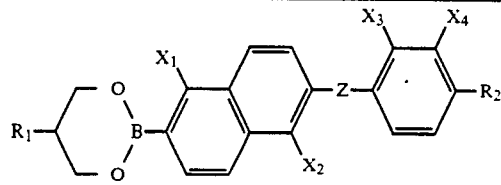

| Example Compound No. | R₁ | X₁ | X₂ | X₃ | X₄ | Z | R₂ |
|---|---|---|---|---|---|---|---|
| 503 | $C_4H_9-$ | H | H | H | F | $-COO-$ | $-COOCH_2C^*H(CH_3)C_2H_5$ |
| 504 | $C_7H_{15}-$ | H | H | Cl | H | " | $-COOC^*H(CH_3)C_6H_{13}$ |
| 505 | $C_{10}H_{21}-$ | H | H | H | H | " | " |
| 506 | $C_8H_{17}-$ | H | H | H | H | " | $-O(CH_2)_4C^*H(CH_3)C_2H_5$ |
| 507 | $C_{11}H_{23}-$ | H | H | H | H | " | $-OCH_2C^*H(OC_4H_9)CH_3$ |
| 508 | $C_{14}H_{29}-$ | H | H | H | $-C_2H_5$ | " | $-CH_2C^*H(CH_3)C_2H_5$ |

EXAMPLES

Now, the present invention will be described in detail in accordance with examples, but needless to say, the purport and the applied scope of the present invention should not be limited to these examples.

In tables given below, the symbol C represents a crystal phase, SC* represents a chiral smectic C phase, SA represents a smectic A phase, Ch represents a cholesteric (chiral nematic) phase, I represents an isotropic liquid, and SX represents an unknown smectic phase. Further, the symbol "." of each phase and a numeral on its right side indicate a phase transition temperature from this phase to a phase on its right side, and the symbol "-" means that the compound does not show its phase. Furthermore, a value in each pair of round parentheses represents a monotropic phase transition temperature, and the symbol "*" represents an asymmetric carbon atom.

EXAMPLE 1

Preparation of (R)—6-benzyloxynaphthalene-2-carboxylic acid 1'-methylheptyl ester In 500 ml of benzene, 65 g of 6-benzyloxynaphthalene-2-carboxylic acid was heated at reflux together with 50 g of oxalyl chloride for a period of 4 hours, and afterward the excessive oxalyl chloride and benzene were distilled out under reduced pressure in order to obtain an acid chloride. This acid chloride was then dissolved in 100 ml of benzene, and to the resulting solution was added a solution in which 30 g of (R)—2-octanol was dissolved in 30 ml of pyridine. Then, the mixed solution was allowed to stand at room temperature for 8 hours. A precipitated pyridine hydrochloride was filtered out, and an organic layer was then washed with a 2N hydrochloric acid solution and a 2N aqueous sodium hydroxide solution. Further, water washing was then carried out until the solution had become neutral. The organic layer was separated and then dried with anhydrous magnesium sulfate, and the used benzene was distilled out under reduced pressure. The resulting residue was recrystallized out of ethanol in order to prepare 80 g of the desired (R)—6-benzyloxynaphthalene-2-carboxylic acid 1'-methylheptyl ester.

A phase transition temperature of this compound is set forth in Table 3.

Analytical values of elements constituting this compound are closely in accord with theoretical values, as follows:

| Theoretical Value (as $C_{26}H_{30}O_3$) | Analytical Value |
|---|---|
| C | 79.96% | 79.89% |
| H | 7.74% | 7.70% |

EXAMPLE 2 TO 8

The same procedure as in Example 1 was repeated with the exception that (R)-2-octanol was replaced with various optically active alcohols, in order to prepare various optically active 6-benzyloxynaphthalene-2-carboxylic acid alkyl esters. Their phase transition temperatures which are physical values are set forth in Table 3.

EXAMPLE 9

Preparation of
(R)-6-(4'-decyloxyphenylcarbonyloxy)-2-naphthalenecarboxylic acid 1''-methylheptyl ester (i) First, 30 g of (R)—6-benzyloxynaphthalene-2-carboxylic acid 1'-methylheptyl ester prepared in Example 1 was dissolved in 200 ml of ethanol, and hydrogenation was then carried out at 40° C. under atmospheric pressure in the presence of 4 g of a 5% palladium/carbon composite. The latter was then filtered out, and the used solvent was distilled out under reduced pressure in order to prepare 23 g of a benzyl group-free product having a melting point of 67° to 68° C.

(ii) Next, 4.0 g of (R)—6-hydroxynaphthalene-2-carboxylic acid 1-methylheptyl ester which was the product of the preceding paragraph (i), 3.7 g of 4-decyloxybenzoic acid, 2.6 g of N,N'-dicyclohexylcarbodiimide and 10 mg of 4-pyrrolidinopyridine were dissolved in 50 ml of chloroform, and the resulting mixture was then allowed to stand at room temperature for 8 hours. A secondarily produced N,N'-dicyclohexyl urea was filtered out, and an organic layer was then washed with a 2N hydrochloric acid solution and a 2N aqueous sodium hydroxide solution, followed by water washing. The organic layer was then dried with anhydrous magnesium sulfate, and the used solvent was distilled out to prepare a crude product. The latter was then purified by the use of a silica gel column chromatography utilizing benzene as an eluent. Further, recrystallization was accomplished out of ethanol to prepare 5.0 g of the desired (R)—6-(4'-decyloxyphenylcarbonyloxy-2-naphthalenecarboxylic acid 1''-methylheptyl ester in the state of a colorless needle crystal. The yield was 67%. A phase transition temperature of the thus prepared compound is set forth in Table 3. Analytical values of elements constituting this compound are closely in accord with theoretical values, as follows:

| Theoretical Value (as $C_{36}H_{48}O_5$) | Analytical Value |
|---|---|
| C | 77.11% | 77.25% |

| Theoretical Value (as $C_{36}H_{48}O_5$) | Analytical Value |
|---|---|
| H | 8.63% | 8.59% |

When measured at a 10° C lower temperature than an SC*-SA phase transition temperature, a value of a spontaneous polarization (Ps) was 87 nC/cm$^2$.

EXAMPLES 10 TO 19

The same procedure as in the process (ii) in Example 9 was repeated with the exception that 4-decyloxybenzoic acid was replaced with various 4-alkyloxybenzoic acids, 4-alkylbenzoic acids or 4-alkyloxy-3-halogenobenzoic acids, in order to thereby prepare various ester compounds. Their phase transition temperatures which are physical values are all set forth in Table 3.

EXAMPLES 20 TO ↓

Various ester compounds were prepared in a manner similar to that of Example 9 (ii) from various optically active 6-hydroxynaphthalene-2-carboxylic acid alkyl esters or various optically active 6-hydroxy-5-halogenonaphthalene2-carboxylic acid alkyl esters prepared in a manner similar to that of Example 9 (i) and various 4-alkoxybenzoic acids, 4-alkoxy-3-halogenobenzoic acids or optically active 4-alkoxybenzoic acids. Their phase transition temperatures which are physical values are set forth in Table 3.

EXAMPLE 76

Preparation of
(s)—6-(2'-methylbutyloxy)—2-naphthyl-4''-decyloxybenzoic acid ester To 50 ml of methylene chloride were added 1.0 g of 4-decyloxybenzoic acid, 750 mg of (s)—6-(2 -methylbutyloxy)-2-naphthol, 700 mg of N,N'-dicyclohexylcarbodiimide and 20 mg of 4-pyrrolidinopyridine, and the resulting mixture was then allowed to stand at room temperature for 4 hours. Secondarily produced N,N'-dicyclohexyl urea was filtered out, and an organic layer was then washed with a 5% hydrochloric acid solution, a 5% aqueous sodium hydroxide solution and water in this order, followed by drying with anhydrous magnesium sulfate. Methylene chloride was then distilled out, and the resulting residue was purified by the use of a silica gel column chromatography utilizing benzene as an eluent. The thus obtained crystal was recrystallized twice out of ethanol to prepare 750 mg of the desired (s)-6-(2'-methylbutyloxy)-2-naphthyl-4''-decyloxybenzoic acid ester in the state of a colorless needle crystal. The yield was 47%. A phase transition temperature of the thus prepared compound is set forth in Table 3. Analytical values of elements constituting this compound are closely in accord with theoretical values, as follows:

| Theoretical Value (as $C_{32}H_{42}O_4$) | Analytical Value |
|---|---|
| C | 78.33% | 78.41% |
| H | 8.63% | 8.72% |

When measured at a 10° C. lower temperature than an SC*-SA transition temperature, a value of a spontaneous polarization (Ps) was 2 nC/cm$^2$.

EXAMPLES 77 TO 86

The same procedure as in Example 76 was repeated with the exception that 4-decyloxybenzoic acid was replaced with various 4-alkoxybenzoic acids or 4-alkylbenzoic acids in order to prepare optically active various ester compounds. Their phase transition temperatures which are physical values are set forth in Table 3.

EXAMPLES 87 TO 110

Following the same procedure as in Example 76, various optically active 6-alkyloxy-2-naphthol or optically active 6-alkoxyalkyloxy-2-naphthols were reacted with 4-alkoxybenzoic acids, and various 6-alkoxy-2-naphthols were reacted with optically active 4-alkoxybenzoic acids, in order to prepare various optically active esters. Their phase transition temperatures which are physical values are set forth in Table 3.

EXAMPLE 111

Preparation of (s)—4'-(2"-methylbutyloxy)phenyl-6-octyloxynaphthalene-2-carboxylic acid ester In 50 ml of methylene chloride were dissolved 1.8 g of 6-octyloxynaphthalene-2-carboxylic acid, 1.1 g of (s)-4-(2'-methylbutyloxy)phenol, 1.2 g of N,N'-dicyclohexylcarbodiimide and 50 mg of 4-pyrrolidinopyridine, and the resulting mixture was then allowed to stand at room temperature for 15 hours. Secondarily produced N,N'-dicyclohexyl urea was filtered out, and an organic layer was then washed with a 5% hydrochloric acid solution, a 5% aqueous sodium hydroxide solution and water in this order, followed by drying with anhydrous magnesium sulfate. Methylene chloride was distilled out, and the resulting residue was then purified by the use of a silica gel column chromatography utilizing benzene as an eluent. The thus obtained crystal was recrystallized twice out of ethanol to prepare the desired (s)-4'-2"-methylbutyloxy)phenyl-6-octyloxynaphthalene-2-carboxylic acid ester in the state of a colorless needle crystal. The yield was 59%.

A phase transition temperature of the thus prepared compound is set forth in Table 3. Analytical values of elements constituting this compound are closely in accord with theoretical values, as follows:

| Theoretical Value (as $C_{30}H_{38}O_4$) | | Analytical Value |
| --- | --- | --- |
| C | 77.89% | 77.95% |
| H | 8.28% | 8.20% |

EXAMPLES 112 AND 113

The same procedure as in Example 111 was repeated with the exception that 4-octyloxybenzoic acid was replaced with various 4-alkoxybenzoic acids in order to prepare ester compounds. Their phase transition temperatures which are physical values are set forth in Table 3.

EXAMPLES 114 TO 131

Following the same procedure as in Example 111, optically active 4-alkoxyphenols or optically active 4-alkylphenols were reacted with various 6-alkoxynaphthalene-2-carboxylic acid, or various 4-alkoxyphenols were reacted with various optically active 6-alkoxynaphthalene-2-carboxylic acids or 4-halogenophenols, or 4-cyanophenol or 3-halogeno-4-cyanophenols were reacted with optically active 6-alkoxynaphthalene-2-carboxylic acids, in order to prepare various esters. Their phase transition temperatures which are physical values are set forth in Table 3.

EXAMPLES 132

Preparation of (s)-4-(6'-octyloxy-2'-naphthoyloxy)benzoic acid 2"-methylbutyl ester In 30 ml of methylene chloride were dissolved 700 mg of (s)-4-hydroxybenzoic acid 2'-methylbutyl ester, 1.0 g of 6-octyloxynaphthalene-2-carboxylic acid, 700 mg of N,N'-dicyclohexylcarbodiimide and 20 mg of 4-pyrrolidinopyridine, and the resulting mixture was then allowed to stand at room temperature for 10 hours. Secondarily produced N,N'-dicyclohexyl urea was filtered out, and an organic layer was then washed with a 5% hydrochloric acid solution, a 5% aqueous sodium hydroxide solution and water in this order, followed by drying with anhydrous magnesium sulfate. Methylene chloride was distilled out, and the resulting residue was then purified by the use of a silica gel column chromatography utilizing benzene as an eluent. The thus obtained crystal was recrystallized out of ethanol to prepare 1.1 g of the desired (s)-4-(6'-octyloxy-2'-naphthoyloxy)benzoic acid 2"-methylbutyl ester in the state of a colorless needle crystal. The yield was 67%.

A phase transition temperature of the thus prepared compound is set forth in Table 3. Analytical values of elements constituting this compound are closely in accord with theoretical values, as follows:

| Theoretical value (as $C_{31}H_{38}O_5$) | | Analytical Value |
| --- | --- | --- |
| C | 75.89% | 75.75% |
| H | 7.81% | 7.79% |

EXAMPLES 133 TO 135

The same procedure as in Example 132 was repeated with the exception that 6-octyloxynaphthalene-2-carboxylic acid was replaced with various 6-alkyloxynaphthalene-2-carboxylic acids in order to prepare various ester compounds. Their phase transition temperatures which are physical values are set forth in Table 3.

EXAMPLES 136 TO 151

Following the same procedure as in Example 132, various optically active 4-hydroxybenzoic acid alkyl esters were reacted with various 6-alkoxynaphthalene-2-carboxylic acids or 6-alkoxyalkyloxynaphthalene-2-carboxylic acids in order to prepare various ester compound. Their phase transition temperatures which are physical values are set forth in Table 3.

TABLE 3

Structure: naphthalene with X at position 1, A at position 2, B at position 6.

| Example Number | Wherein A represents | Wherein B represents | X | Phase transition temperature (°C.) C | SC* | SA | Ch | I |
|---|---|---|---|---|---|---|---|---|
| 1 | C₆H₅-CH₂O- | -C(=O)-O-*CH(CH₃)C₆H₁₃ | H | • 69.5 | — | — | — | • |
| 2 | " | -C(=O)-O-*CH(CH₃)C₃H₇ | H | • 87.0 | — | — | — | • |
| 3 | " | -C(=O)-O-*CH(CH₃)C₂H₅ | H | • 60.5 | — | — | — | • |
| 4 | " | -C(=O)-OCH₂*CH(CH₃)C₂H₅ | H | • 78.5 | — | — | — | • |
| 5 | " | -C(=O)-O(CH₂)₂*CH(CH₃)C₂H₅ | H | • 65.0 | — | — | — | • |
| 6 | " | -C(=O)-O(CH₂)₂*CH(CH₃)(CH₂)₃CH(CH₃)₂ | H | • 51.5 | — | — | — | • |
| 7 | C₆H₅-CH₂O- | -C(=O)-O(CH₂)₃*CH(CH₃)C₂H₅ | H | • 58.4 | — | — | — | • |
| 8 | " | -C(=O)-O(CH₂)₅*CH(CH₃)C₂H₅ | H | <10 | | | | |
| 9 | C₁₀H₂₁O-C₆H₄-C(=O)-O- | -C(=O)-O-*CH(CH₃)C₆H₁₃ | H | • 46.5 | (• 41.5) | • 64.6 | — | • |
| 10 | C₄H₉O-C₆H₄-C(=O)-O- | " | H | • 97.0 | — | — | — | • |
| 11 | C₈H₁₇O-C₆H₄-C(=O)-O- | " | H | • 53.8 | — | • 66.7 | — | • |
| 12 | C₉H₁₉O-C₆H₄-C(=O)-O- | " | H | • 63.0 | (• 30.0) | • 63.5 | — | • |
| 13 | C₁₁H₂₃O-C₆H₄-C(=O)-O- | -C(=O)-O-*CH(CH₃)C₆H₁₃ | H | • 59.7 | (• 42.5) | • 62.4 | — | • |
| 14 | C₁₂H₂₅O-C₆H₄-C(=O)-O- | " | H | • 50.5 | (• 49.7) | • 63.0 | — | • |

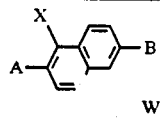

TABLE 3-continued

Structure:

$$\underset{A}{\phantom{x}}\overset{X}{\underset{\phantom{x}}{\text{naphthalene}}}\text{—B}$$

| Example Number | Wherein A represents | Wherein B represents | X | Phase transition temperature (°C.) | | | | |
|---|---|---|---|---|---|---|---|---|
| 29 | $C_{10}H_{21}O$—⌬—C(=O)—O— | " | H | • 57.0 | • 55.5 | • 86.8 | — | • |
| 30 | $C_{11}H_{23}O$—⌬—C(=O)—O— | " | H | • 59.1 | (• 54.5) | • 86.7 | — | • |
| 31 | $C_{12}H_{25}O$—⌬—C(=O)—O— | " | H | • 55.0 | (• 53.0) | • 86.6 | — | • |
| 32 | $C_{14}H_{29}O$—⌬—C(=O)—O— | " | H | • 61.5 | (• 54.5) | • 85.1 | — | • |
| 33 | $C_{16}H_{33}O$—⌬—C(=O)—O— | " | H | • 56.5 | (• 55.0) | • 84.5 | — | • |
| 34 | $C_9H_{19}O$—⌬(F)—C(=O)—O— | —C(=O)—O—*CH(CH$_3$)C$_2$H$_5$ | H | • 55.0 | (• 45.2) | • 77.7 | — | • |
| 35 | $C_{12}H_{25}O$—⌬(F)—C(=O)—O— | " | H | • 50.4 | (• 40.5) | • 73.4 | — | • |
| 36 | $C_4H_9O$—⌬—C(=O)—O— | —C(=O)—OCH$_2$*CH(CH$_3$)C$_2$H$_5$ | H | • 99.5 | — | (• 83.9) | • 100.9 | • |
| 37 | $C_6H_{13}O$—⌬—C(=O)—O— | " | H | • 81.7 | — | • 98.7 | • 105.7 | • |
| 38 | $C_7H_{15}O$—⌬—C(=O)—O— | " | H | • 70.8 | (• 54.6) | • 100.7 | • 101.9 | • |
| 39 | $C_8H_{17}O$—⌬—C(=O)—O— | " | H | • 62.1 | (• 59.0) | • 102.8 | — | • |
| 40 | $C_9H_{19}O$—⌬—C(=O)—O— | " | H | • 60.1 | • 66.9 | • 102.9 | — | • |
| 41 | $C_{10}H_{21}O$—⌬—C(=O)—O— | " | H | • 58.4 | • 66.0 | • 104.0 | — | • |
| 42 | $C_{11}H_{23}O$—⌬—C(=O)—O— | —C(=O)—OCH$_2$*CH(CH$_3$)C$_2$H$_5$ | H | • 70.2 | • 73.7 | • 103.8 | — | • |

TABLE 3-continued

Structure: naphthalene with X at position 1, A at position 2, B at position 6

| Example Number | Wherein A represents | Wherein B represents | X | Phase transition temperature (°C.) |
|---|---|---|---|---|
| 43 | $C_{12}H_{25}O$—⌬—C(=O)—O— | " | H | • 77.2  (• 71.3)  • 104.0  —  • |
| 44 | $C_{13}H_{27}O$—⌬—C(=O)—O— | " | H | • 67.6  • 73.5  • 103.4  —  • |
| 45 | $C_{14}H_{29}O$—⌬—C(=O)—O— | " | H | • 59.8  • 63.6  • 102.1  —  • |
| 46 | $C_{15}H_{31}O$—⌬—C(=O)—O— | " | H | • 58.6  • 66.4  • 102.1  —  • |
| 47 | $C_{16}H_{33}O$—⌬—C(=O)—O— | " | H | • 65.6  • 58.1  • 100.1  —  • |
| 48 | $C_{18}H_{37}O$—⌬—C(=O)—O— | " | H | • 59.5  • 64.0  • 99.7  —  • |
| 49 | $C_4H_9O$—⌬(F)—C(=O)—O— | " | H | • 114.5  —  —  —  • |
| 50 | $C_8H_{17}O$—⌬(F)—C(=O)—O— | —C(=O)—OCH$_2$CH(CH$_3$)C$_2$H$_5$ | H | • 73.0  (• 38.8)  • 92.8  —  • |
| 51 | $C_9H_{19}O$—⌬(F)—C(=O)—O— | " | H | • 74.3  (• 50.8)  • 92.5  —  • |
| 52 | $C_{10}H_{21}O$—⌬(F)—C(=O)—O— | " | H | • 64.0  (• 57.4)  • 91.8  —  • |
| 53 | $C_{12}H_{25}O$—⌬(F)—C(=O)—O— | " | H | • 63.9  (• 57.5)  • 94.5  —  • |
| 54 | $C_{16}H_{33}O$—⌬(F)—C(=O)—O— | " | H | • 57.4  • 58.1  • 89.0  —  • |
| 55 | $C_8H_{17}O$—⌬(Cl)—C(=O)—O— | " | H | • 103.1  —  —  —  • |

TABLE 3-continued
| Example Number | Wherein A represents | Wherein B represents | X | Phase transition temperature (°C.) | | | | |
|---|---|---|---|---|---|---|---|---|
| 56 | 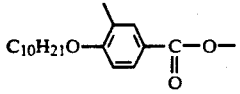 | 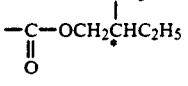 | H | • 73.7 | — | (• 66.2) | — | • |
| 57 | 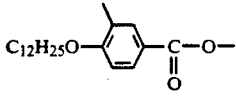 | " | H | • 52.8 | — | • 70.5 | — | • |
| 58 | 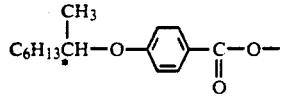 | " | H | • 57.5 | — | — | — | • |
| 59 | 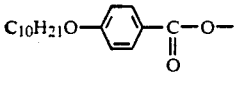 | 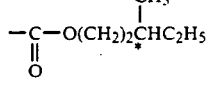 | H | • 56.3 | • 73.0 | • 103.3 | — | • |
| 60 | 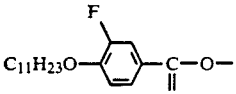 | " | H | • 68.8 | (• 67.0) | • 90.3 | — | • |
| 61 | 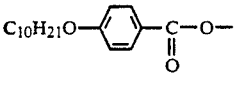 | 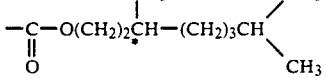 | H | • 72.0 | (• 68.5) | • 91.0 | — | • |
| 62 | 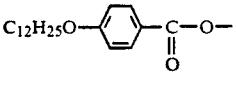 | " | H | • 75.0 | (• 74.3) | • 88.0 | — | • |
| 63 | 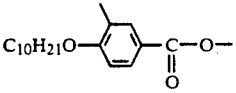 | 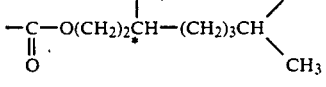 | H | • 49.5 | — | — | — | • |
| 64 | 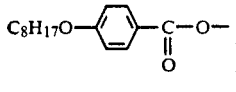 | 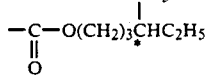 | H | • 66.6 | • | • 100.5 | — | • |
| 65 | 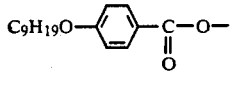 | " | H | • 52.5 | • 64.0 | • 99.2 | — | • |
| 66 |  | " | H | • 51.6 | • 73.0 | • 99.1 | — | • |
| 67 |  | " | H | • 54.2 | • 78.5 | • 99.7 | — | • |
| 68 | 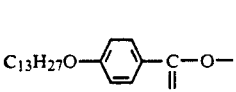 | " | H | • 64.3 | • 80.5 | • 101.3 | — | • |
| 69 |  | " | H | • 64.9 | • 80.5 | • 98.6 | — | • |

TABLE 3-continued

Structure: naphthalene with X at position 1, A at position 2, B at position 6.

| Example Number | Wherein A represents | Wherein B represents | X | Phase transition temperature (°C.) | | | | |
|---|---|---|---|---|---|---|---|---|
| 70 | $C_{14}H_{29}O$—⌬—C(=O)—O— | " | H | • 58.0 | • 82.9 | • 98.5 | — | • |
| 71 | $C_{15}H_{31}O$—⌬—C(=O)—O— | —C(=O)—O(CH$_2$)$_3$*CH(CH$_3$)C$_2$H$_5$ | H | • 67.7 | • 79.5 | • 98.8 | — | • |
| 72 | $C_{12}H_{25}O$—⌬(F)—C(=O)—O— | " | H | • 58.7 | • 75.9 | • 88.9 | — | • |
| 73 | $C_{12}H_{25}O$—⌬—C(=O)—O— | —C(=O)—O(CH$_2$)$_5$*CH(CH$_3$)C$_2$H$_5$ | H | • 54.5 | • 90.0 | • 100.3 | — | • |
| 74 | $C_{10}H_{21}O$—⌬—C(=O)—O— | —C(=O)—OCH$_2$*CH(CH$_3$)C$_2$H$_5$ | Cl | • 47.5 | — | • 59.5 | • 68.9 | • |
| 75 | $C_{14}H_{29}O$—⌬—C(=O)—O— | " | Cl | • 48.2 | — | • 72.1 | — | • |
| 76 | $C_{10}H_{21}O$—⌬—C(=O)—O— | —O—CH$_2$—*CH(CH$_3$)C$_2$H$_5$ | H | • 64.5 | • 77.1 | • 85.5 | • 98.7 | • |
| 77 | $C_6H_{13}O$—⌬—C(=O)—O— | " | H | • 85.1 | — | — | • 100.7 | • |
| 78 | $C_8H_{17}O$—⌬—C(=O)—O— | —OCH$_2$*CH(CH$_3$)C$_2$H$_5$ | H | • 77.2 | (• 71.2) | — | • 102.8 | • |
| 79 | $C_9H_{19}O$—⌬—C(=O)—O— | " | H | • 62.0 | • 76.1 | • 76.9 | • 98.0 | • |
| 80 | $C_{11}H_{23}O$—⌬—C(=O)—O— | " | H | • 68.0 | • 79.2 | • 89.0 | • 96.5 | • |
| 81 | $C_{12}H_{25}O$—⌬—C(=O)—O— | " | H | • 67.2 | • 76.9 | • 91.6 | • 97.0 | • |
| 82 | $C_{13}H_{27}O$—⌬—C(=O)—O— | " | H | • 74.3 | • 78.5 | • 92.7 | • 95.5 | • |
| 83 | $C_{14}H_{29}O$—⌬—C(=O)—O— | " | H | • 73.3 | • 75.3 | • 93.7 | • 95.0 | • |

TABLE 3-continued

Structure: A-[naphthalene with X at position 1]-B

| Example Number | Wherein A represents | Wherein B represents | X | Phase transition temperature (°C.) | | | | |
|---|---|---|---|---|---|---|---|---|
| 84 | $C_{15}H_{31}O$-⌬-C(=O)-O- | " | H | • 79.1 | (• 73.0) | • 93.4 | • 94.0 | • |
| 85 | $C_{16}H_{33}O$-⌬-C(=O)-O- | " | H | • 80.3 | — | • 93.0 | — | • |
| 86 | $C_8H_{17}$-⌬-C(=O)-O- | " | H | • 71.7 | — | — | (• 67.2) | • |
| 87 | $C_6H_{13}O$-⌬-C(=O)-O- | -O(CH$_2$)$_3$$\overset{*}{C}$HC$_2$H$_5$ (CH$_3$) | H | • 82.3 | — | — | • 117.1 | • |
| 88 | $C_8H_{17}O$-⌬-C(=O)-O- | " | H | • 71.2 | • 72.6 | — | • 114.6 | • |
| 89 | $C_{10}H_{21}O$-⌬-C(=O)-O- | " | H | • 67.7 | • 89.0 | — | • 110.8 | • |
| 90 | $C_{12}H_{25}O$-⌬-C(=O)-O- | " | H | • 67.0 | • 94.3 | • 95.2 | • 106.0 | • |
| 91 | $C_{14}H_{29}O$-⌬-C(=O)-O- | " | H | • 73.1 | • 94.7 | • 99.4 | • 103.3 | • |
| 92 | $C_{16}H_{33}O$-⌬-C(=O)-O- | " | H | • 79.0 | • 92.7 | • 99.1 | • 101.0 | • |
| 93 | $C_8H_{17}$-⌬-C(=O)-O- | " | H | • 80.3 | — | — | • 86.4 | • |
| 94 | $C_7H_{15}O$-⌬-C(=O)-O- | -O$\overset{*}{C}$HC$_6$H$_{13}$ (CH$_3$) | H | • 57.7 | — | — | (• 54.8) | • |
| 95 | $C_8H_{17}O$-⌬-C(=O)-O- | " | H | • 41.5 | • 47.8 | — | • 59.4 | • |
| 96 | $C_9H_{19}O$-⌬-C(=O)-O- | " | H | • 60.0 | (• 49.1) | — | (• 58.0) | • |
| 97 | $C_{10}H_{21}O$-⌬-C(=O)-O- | " | H | • 65.2 | — | — | — | • |
| 98 | $C_{11}H_{23}O$-⌬-C(=O)-O- | " | H | • 58.0 | (• 50.0) | • 58.9 | • 61.0 | • |

TABLE 3-continued

Structure: A-naphthalene(X)-B where X is at position 1, A at position 2, B at position 6.

| Example Number | Wherein A represents | Wherein B represents | X | Phase transition temperature (°C.) |
|---|---|---|---|---|
| 99 | $C_{12}H_{25}O$—C₆H₄—C(=O)—O— | " | H | • 57.3  (• 56.2)  • 61.7  • 62.0  • |
| 100 | $C_{13}H_{27}O$—C₆H₄—C(=O)—O— | " | H | • 48.5  • 53.0  • 63.5  —  • |
| 101 | $C_{14}H_{29}O$—C₆H₄—C(=O)—O— | " | H | • 53.5  • 56.8  • 65.1  —  • |
| 102 | $C_{12}H_{25}O$—C₆H₄—C(=O)—O— | —OCH(CH₃)C₃H₇* | H | • 52.5  • 54.7  —  • 59.5  • |
| 103 | $C_9H_{19}O$—C₆H₄—C(=O)—O— | —OCH(CH₃)C₂H₅* | H | • 61.7  (• 50.5)  —  • 62.1  • |
| 104 | $C_{10}H_{21}O$—C₆H₄—C(=O)—O— | " | H | • 57.3  (• 54.7)  • 57.2  • 60.3  • |
| 105 | $C_8H_{17}O$—C₆H₄—C(=O)—O— | —OCH₂CH(OC₂H₅)CH₃* | H | • 62.2  —  • 65.8  • 80.1  • |
| 106 | $C_{12}H_{25}O$—C₆H₄—C(=O)—O— | " | H | • 50.5  • 68.1  • 76.5  • 78.0  • |
| 107 | $C_9H_{19}O$—C₆H₄—C(=O)—O— | —OCH₂CH(OC₃H₇)CH₃* | H | • 64.6  • 56.5  • 65.5  • 72.8  • |
| 108 | CH₃-C₂H₅*CHCH₂O—C₆H₄—C(=O)—O— | —OC₁₀H₂₁ | H | • 76.3  —  —  • 98.4  • |
| 109 | CH₃-C₆H₁₃*CHO—C₆H₄—C(=O)—O— | —OC₁₀H₂₁ | H | • 43.1  —  —  • 54.3  • |
| 110 | CH₃-C₂H₅*CH(CH₂)₃O—C₆H₄—C(=O)—O— | —OC₁₀H₂₁ | H | • 61.5  • 74.1  —  • 113.1  • |
| 111 | $C_8H_{17}O$— | —C(=O)—O—C₆H₄—OCH₂*CH(CH₃)C₂H₅ | H | • 100.6  —  • 108.3  • 108.7  • |
| 112 | $C_6H_{13}O$— | " | H | • 101.6  —  (• 98.8)  • 108.9  • |
| 113 | $C_{10}H_{21}O$— | " | H | • 103.0  —  • 109.5  —  • |
| 114 | $C_6H_{13}O$— | —C(=O)—O—C₆H₄—O(CH₂)₃*CH(CH₃)C₂H₅ | H | • 74.5  • 80.4  • 99.5  • 117.8  • |
| 115 | $C_8H_{17}O$ | " | H | • 73.6  • 84.0  • 111.1  • 116.8  • |

TABLE 3-continued

Structure: naphthalene with substituents A (position 2), B (position 6), X (position 1)

| Example Number | A represents | B represents | X | Phase transition temperature (°C.) |
|---|---|---|---|---|
| 116 | C₁₀H₂₁O | " | H | • 60.6  • 93.6  • 114.9  —  • |
| 117 | C₁₂H₂₅O | " | H | • 55.5  • 96.1  • 114.1  —  • |
| 118 | C₁₄H₂₉O | " | H | • 62.0  • 94.8  • 110.8  —  • |
| 119 | C₄H₉O— | —C(=O)—O—C₆H₄—CH₂CH(CH₃)C₂H₅ | H | • 37.7  —  —  • 41.0  • |
| 120 | C₇H₁₅O— | " | H | • 42.5  —  —  (• 37.8)  • |

|  |  |  |  | C | SA | Ch | I |
|---|---|---|---|---|---|---|---|
| 121 | (CH₃)(C₂H₅)CHCH₂O— | —C(=O)—O—C₆H₄—OC₆H₁₃ | H | • 84.6 | — | • 96.9 | • |
| 122 | " | —C(=O)—O—C₆H₄—OC₈H₁₇ | H | • 81.5 | — | • 96.0 | • |
| 123 | " | —C(=O)—O—C₆H₄—OC₁₀H₂₁ | H | • 79.9 | — | • 94.2 | • |
| 124 | " | —C(=O)—O—C₆H₄—OC₁₂H₂₅ | H | • 79.6 | — | • 91.0 | • |
| 125 | (CH₃)(C₂H₅)CH(CH₂)₃O— | —C(=O)—O—C₆H₄—OC₆H₁₃ | H | • 87.6 | • 98.1 | • 113.0 | • |
| 126 | " | —C(=O)—O—C₆H₄—OC₈H₁₇ | H | • 71.8 | • 84.5 | • 110.7 | • |
| 127 | " | —C(=O)—O—C₆H₄—OC₁₀H₂₁ | H | • 73.7 | • 87.9 | • 108.8 | • |
| 128 | " | —C(=O)—O—C₆H₄—OC₁₂H₂₅ | H | • 71.4 | • 78.4 | • 104.7 | • |
| 129 | (CH₃)(C₆H₁₃)CHO— | —C(=O)—O—F | H | • 52.0 | — | — | • |
| 130 | " | —C(=O)—O—CN | H | • 35.7 | — | — | • |
| 131 | " | —C(=O)—O—C₆H₃(F)—CN | H | <10 | | | |

|  |  |  |  | C | SC* | SA | I |
|---|---|---|---|---|---|---|---|
| 132 | C₈H₁₇O— | —C(=O)—O—C(=O)—OCH₂CH(CH₃)C₂H₅ | H | • 69.4 | — | • 103.9 | • |
| 133 | C₁₀H₂₁O— | " | H | • 85.2 | — | • 103.6 | • |
| 134 | C₁₂H₂₅O— | " | H | • 63.4 | — | • 101.4 | • |
| 135 | C₁₄H₂₉O— | " | H | • 62.3 | — | • 99.4 | • |

TABLE 3-continued $$\underset{A}{\overset{X}{\text{naphthalene}}}-B$$

| Example Number | Wherein A represents | Wherein B represents | X | Phase transition temperature (°C.) | | | |
|---|---|---|---|---|---|---|---|
| 136 | C₁₀H₂₁O— | —C(=O)—O—C(=O)—*OCH(CH₃)C₃H₇ | H | • 52.0 | — | • 73.2 | • |
| 137 | C₁₂H₂₅O— | " | H | • 57.3 | — | • 71.0 | • |
| 138 | C₆H₁₃O— | —C(=O)—O—⟨C₆H₄⟩—C(=O)—*O(CH₂)₃CH(CH₃)C₂H₅ | H | • 79.5 | — | • 101.4 | • |
| 139 | C₈H₁₇O— | " | H | • 82.8 | — | • 100.9 | • |
| 140 | C₁₀H₂₁O— | " | H | • 74.7 | — | • 100.2 | • |
| 141 | C₁₂H₂₅O— | " | H | • 59.5 | • 68.0 | • 102.6 | • |
| 142 | C₁₄H₂₉O— | " | H | • 68.5 | (• 64.9) | • 95.5 | • |
| 143 | C₁₆H₃₃O— | " | H | • 55.8 | • 60.3 | • 88.0 | • |
| 144 | C₁₂H₂₅O— | —C(=O)—O—⟨C₆H₄⟩—C(=O)—O—*CH(CH₃)C₂H₅ | H | • 62.3 | — | • 73.5 | • |
| 145 | C₄H₉O—(CH₂)₂O— | " | H | • 47.0 | — | • 52.5 | • |
| 146 | C₈H₁₇O— | —C(=O)—O—⟨C₆H₄⟩—C(=O)—*OCH(CH₃)C₄H₉ | H | • 55.5 | — | • 68.7 | • |
| 147 | C₉H₁₉O— | " | H | • 61.7 | — | • 67.5 | • |
| 148 | C₁₀H₂₁O— | " | H | • 57.7 | — | • 67.7 | • |
| 149 | C₇H₁₅O— | —C(=O)—O—⟨C₆H₄⟩—C(=O)—*OCH(CH₃)C₅H₁₁ | H | • 60.3 | — | • 65.3 | • |
| 150 | C₉H₁₉O— | " | H | • 63.7 | — | • 64.8 | • |
| 151 | C₁₁H₂₃O— | " | H | • 54.8 | — | • 64.9 | • |

EXAMPLE 152

Preparation of (s)-6-(4'''-octyloxybiphenyl-4'-carbonyl)-2-naphthalenecarboxylic acid 2'''-methylbutyl ester In 300 ml of benzene, 5.0 g of 4'-octyloxybiphenyl-4-carboxylic acid and 20 ml of thionyl chloride were heated at reflux temperature for 5 hours, and afterward the excessive thionyl chloride and benzene were distilled out under reduced pressure. To carboxylic acid chloride of the residual were added 4.0 of (s)-6-hydroxynaphthalene-2-carboxylic acid 2''-methylbutyl ester, 30 ml of pyridine and 300 ml of benzene, and the resulting mixture was heated at reflux for 5 hours. After the mixture had been cooled to room temperature, pyridine hydrochloride was filtered out, and an obtained filtrate was then washed with water, a 10% hydrochloric acid solution, a saturated aqueous NaHCO₃ solution and water in this order, followed by drying with anhydrous magnesium sulfate. After the removal of benzene by distillation, the resulting residue was then separated and purified by the sue of a silica gel column chromatography utilizing benzene as an eluent. The thus obtained crystal was recrystallized out of ethanol-ethyl acetate to prepare 4.5 g of the desired (s)-6-(4'''-octyloxybiphenyl-4'-carbonyloxy)-2-naphthalenecarboxylic acid 2''-methylbutyl ester in the state of a colorless crystal. The yield was 52%. A phase transition temperature of the thus prepared compound is set forth in Table 4. Analytical values of elements constituting this compound are closely in accord with theoretical values, as follows:

| Theoretical Value (as C₃₇H₄₂O₅) | Analytical Value |
|---|---|
| C | 78.41% | 78.50% |
| H | 7.47% | 7.43% |

When measured at a 10° C. lower temperature than an SC*-SA transition temperature, a value of a spontaneous polarization (Ps) was 5 nC/cm².

EXAMPLES 153 TO 164

The same procedure as in Example 152 was repeated with the exception that 4'-octyloxybiphenyl-4-carboxylic acid was replaced with various 4'-alkyloxybiphenyl-4-carboxylic acids, 4'-alkylbiphenyl-4-carboxylic acids or 3'-halogeno-4'-alkyloxybiphenyl-4-carboxylic acids, or that 6-hydroxynaphthalene-2-carboxylic acid 2''-methylbutyl ester was replaced with various optically active 5-halogeno-6-hydroxynaphthalene-2-carboxyl acid alkyl esters or optically active 6-hydroxynaphthalene-2-carboxylic acid alkyl esters, in order to prepare various optically active ester compounds. Their phase transition temperatures which are physical values are set forth in Table 4.

EXAMPLE 165

Preparation of (s)-6-(2'-methylbutyloxy)-2-naphthyl-4''-octyloxybiphenyl-4'''-carboxylic acid ester To 30 ml of methylene chloride were added 400 mg of 4'-octyloxybiphenyl-4-carboxylic acid, 290 mg of (s)-6-(2'-methylbutyloxy)—2-naphthol, 260 mg of N,N'-dicyclohexylcarbodiimide and 20 mg of 4-pyrrolidinopyridine, and the resulting mixture was then allowed to stand at room temperature for 20 hours. A secondarily produced N,N'-dicyclohexyl urea was then filtered out, and an organic layer was washed with a 5% hydrochloric acid solution, a 5% aqueous sodium hydroxide solution and water in this order, followed by drying with anhydrous magnesium sulfate.

After the removal of methylene chloride by distillation, the resulting residue was then purified by the use of a silica gel column chromatography utilizing benzene as an eluent. The thus obtained crystal was recrystallized out of ethanol-ethyl acetate to prepare 280 mg of the desired 6-((s)-2'-methylbutyloxy)—2-naphthyl-4''-octyloxybiphenyl-4'''-carboxylic acid ester in the state of a colorless needle crystal. The yield was 42%. A phase transition temperature of the thus prepared compound is set forth in Table 4. Analytical values of elements constituting this compound are closely in accord with theoretical values, as follows:

| Theoretical Value (as $C_{36}H_{42}O_4$) | | Analytical Value |
|---|---|---|
| C | 80.26% | 80.07% |
| H | 7.86% | 7.85% |

When measured at a 10° C lower temperature than an SC*-SA transition temperature, a value of a spontaneous polarization Ps) was 2 $nC/cm^2$.

EXAMPLES 166 TO 170

The same procedure as in Example 165 was repeated with the exception that 4'-octyloxybiphenyl-4-carboxylic acid was replaced with various 4'-alkyloxybiphenyl-4-carboxylic acids or optically active 4'-alkyloxybiphenyl-4-carboxylic acids, and that (s)-6-(2'-methylbutyloxy)—2-naphthol was replaced with various optically active 6-(alkyloxy)—2-naphthols, 6-alkyloxy-2-naphthol or 6-alkyl-2-naphthol in order to prepare various optically active ester compounds. Their phase transition temperatures which are physical values are set forth in Table 4.

TABLE 4

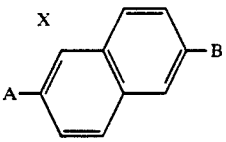

| Example Number | Wherein A represents | Wherein B represents | X | C | SC* | SA | Ch | I |
|---|---|---|---|---|---|---|---|---|
| 152 | 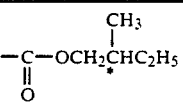 | $-\underset{\underset{O}{\|\|}}{C}-OCH_2\overset{*}{C}HC_2H_5$ with $CH_3$ | H | • 93.7 | • 168.2 | • 247.1 | — | • |
| 153 | " | " | Cl | • 118.7 | (• 97.5) | • 198.4 | • 215.4 | • |
| 154 | 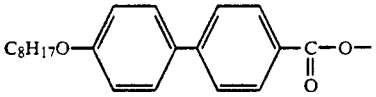 | $-\underset{\underset{O}{\|\|}}{C}-O\overset{*}{C}HC_2H_5$ with $CH_3$ | H | • 107.5 | • 146.5 | • 200.5 | — | • |
| 155 |  | " | H | • 87.0 | • 105.0 | • 185.5 | — | • |
| 156 | 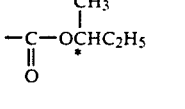 | " | H | • 78.5 | • 117.0 | • 183.0 | — | • |
| 157 | 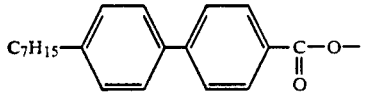 | $-\underset{\underset{O}{\|\|}}{C}-O\overset{*}{C}HC_6H_{13}$ with $CH_3$ | H | • 105.0 | • 127.3 | • 199.5 | — | • |
| 158 | 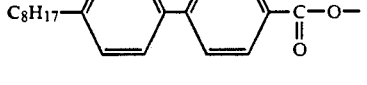 | " | H | • 109.1 | • 147.8 | • 192.4 | — | • |

TABLE 4-continued

Structure:

A—[naphthalene with X at 2-position]—B

| Example Number | Wherein A represents | Wherein B represents | X | C | SC* | SA | Ch | I |
|---|---|---|---|---|---|---|---|---|
| 159 | C₁₀H₂₁O—[biphenyl]—C(=O)O— | " | H | • 111.3 | • 150.5 | • 180.5 | — | • |
| 160 | C₇H₁₅—[biphenyl]—C(=O)O— | —C(=O)—OCH(CH₃)C₆H₁₃ | H | • 72.5 | • 76.5 | • 170.8 | — | • |
| 161 | C₈H₁₇—[biphenyl]—C(=O)O— | " | H | • 85.5 | • 107.1 | • 161.5 | — | • |
| 162 | C₁₀H₂₁—[biphenyl]—C(=O)O— | " | H | • 74.5 | • 127.5 | • 158.5 | — | • |
| 163 | C₉H₁₉O—[biphenyl with Cl]—C(=O)O— | —C(=O)—OCH(CH₃)C₆H₁₃ | H | • 87.5 | • 90.5 | • 169.5 | — | • |
| 164 | C₁₀H₂₁O—[biphenyl with F]—C(=O)O— | " | H | • 90.3 | • 118.0 | • 186.5 | — | • |
| 165 | C₈H₁₇O—[biphenyl]—C(=O)O— | —OCH₂CH(CH₃)C₂H₅ | H | • 147.8 | • 171.0 | • 216.2 | • 230.0 | • |
| 166 | C₂H₅CH(CH₃)CH₂O—[biphenyl]—C(=O)O— | —OC₁₀H₂₁ | H | • 128.1 | • 176.0 | • 183.7 | • 221.8 | • |
| 167 | C₇H₁₅O—[biphenyl]—C(=O)O— | —OCH(CH₃)C₆H₁₃ | H | • 121.0 | — | • 192.3 | • 197.6 | • |
| 168 | C₈H₁₇O—[biphenyl]—C(=O)O— | —OCH(CH₃)C₆H₁₃ | H | • 132.0 | • 138.5 | • 192.5 | • 195.5 | • |
| 169 | C₆H₁₃CH(CH₃)O—[biphenyl]—C(=O)O— | —C₆H₁₃ | H | • 75.0 | • 90.5 | • 110.2 | • 141.0 | • |
| 170 | " | —C₇H₁₅ | H | • 72.7 | • 91.1 | • 112.0 | • 140.0 | • |

EXAMPLE 171

Preparation of (s)-6-(6'-hexyloxynaphthalene-2'-carbonyloxy)naphthalene-2-carboxylic acid 2''-methylbutyl ester In 40 ml of methylene chloride were dissolved 530 mg of 6-hexyloxynaphthalene-2-carboxylic acid, 500 mg of (s)-6-hydroxynaphthalene-2-carboxylic acid 2'-methylbutyl ester, 400 mg of N,N'-dicyclohexylcarbodiimide and 20 mg of 4-pyrrolidinopyridine, and the resulting mixture was then allowed to stand at room temperature for 5 hours. A secondarily produced N,N'-dicyclohexyl urea was then filtered out, and an organic layer was washed with a 5% hydrochloric acid solution, a 5% aqueous sodium hydroxide solution and water in this order, followed by drying with anhydrous magnesium sulfate.

After the removal of methylene chloride by distillation, the resulting residue was then purified by the use of a silica gel column chromatography utilizing benzene as an eluent. The thus obtained crystal was recrystalized out of ethanol-ethyl acetate ester to prepare 580 mg of the desired (s)-6-(6'-hexyloxynaphthalene-2'-carbonyloxy)naphthalene-2-carboxylic acid 2''-methylbutyl ester in the state of a colorless lamellar crystal. The yield was 58%. A phase transition temperature of the thus prepared compound is set forth in Table 5. Analytical values of elements constituting this compound are closely in accord with theoretical values, as follows:

| Theoretical Value (as $C_{33}H_{36}O_5$) | Analytical Value |
|---|---|
| C 77.31% | 77.30% |
| H 7.08% | 7.10% |

EXAMPLES 172 TO 176

The same procedure as in Example 171 was repeated with the exception that 6-hexyloxynaphthalene-2-carboxylic acid was replaced with various 6-alkoxynaphthalene-2-carboxylic acid in order to prepare various optically active ester compounds. Their phase transition temperatures which are physical values are set forth in Table 5.

EXAMPLE 177

Preparation of (s)-6-decyloxy-2-naphthyl-6'-(2''-methylbutyloxy)naphthalene-2'-carboxylic acid ester To 20 ml of methylene chloride were added 300 mg of (s)-6-(2'-methylbutyloxy)naphthalene-2-carboxylic acid, 350 mg of 6-decyloxy-2-naphthol, 240 mg of N,N'-dicyclohexylcarbodiimide and 10 mg of 4-pyrrolidinopyridine, and the resulting mixture was then allowed to stand at room temperature for 3 hours. A secondarily produced N,N'-dicyclohexyl urea was then filtered out, and an organic layer was washed with a 5% hydrochloric acid solution, a 5% aqueous sodium hydroxide solution and water in this order, followed by drying with anhydrous magnesium sulfate.

After the removal of methylene chloride by distillation, the resulting residue was then purified by the use of a silica gel column chromatography utilizing benzene as an eluent. The thus obtained crystal was recrystallized out of ethanol-ethyl acetate to prepare 320 mg of the desired (s)-6-decyloxy-2-naphthyl-6'-(2''-methylbutyloxy)naphthalene-2'-carboxylic acid ester in the state of a colorless needle crystal. The yield was 51%. A phase transition temperature of the thus prepared compound is set forth in Table 5. Analytical values of elements constituting this compound are closely in accord with theoretical values, as follows:

| Theoretical Value (as $C_{36}H_{44}O_4$) | Analytical Value |
|---|---|
| C 79.96% | 80.03% |
| H 8.20% | 8.15% |

EXAMPLE 178

The same procedure as in Example 177 was repeated with the exception that (s)-6-(2'-methylbutyloxy)naphthalene-2-carboxylic acid was replaced with (s)-6-(4'-methylhexyloxy)naphthalene-2-carboxylic acid in order to prepare an optically active ester compound. Its phase transition temperature which is a physical value is set forth in Table 5.

TABLE 5

| Example Number | Wherein A represents | Wherein B represents | X | C | SX | SA | Ch | I |
|---|---|---|---|---|---|---|---|---|
| 171 | $C_6H_{13}O-$ naphthalene $-C(=O)-O-$ | $-C(CH_3)(=O)OCH_2CHC_2H_5^*$ | H | • 133.3 | — | • 152.7 | • 157.4 | • |
| 172 | $C_8H_{17}O-$ naphthalene $-C(=O)-O-$ | " | H | • 82.5 | — | • 152.5 | — | • |

TABLE 5-continued

Structure: naphthalene with X at position 1, A at position 2, B at position 6

| Example Number | Wherein A represents | Wherein B represents | X | C | SX | SA | Ch | I |
|---|---|---|---|---|---|---|---|---|
| 173 | C₁₀H₂₁O-[naphthalene]-C(=O)O- | " | H | • 76.9 | (• 63.1) | • 150.0 | — | • |
| 174 | C₁₂H₂₅O-[naphthalene]-C(=O)O- | " | H | • 91.1 | (• 76.5) | • 147.8 | — | • |
| 175 | C₁₄H₂₉O-[naphthalene]-C(=O)O- | " | H | • 71.8 | (• 66.4) | • 144.4 | — | • |
| 176 | C₁₆H₃₃O-[naphthalene]-C(=O)O- | " | H | • 71.1 | • 76.5 | • 141.5 | — | • |
| 177 | C₂H₅CH(CH₃)CH₂O-[naphthalene]-C(=O)O- (chiral) | —C₁₀H₂₁ | H | • 95.0 | — | — | • 143.3 | • |
| 178 | C₂H₅CH(CH₃)(CH₂)₃O-[naphthalene]-C(=O)O- (chiral) | —C₁₀H₂₁ | H | • 85.7 | • 107.5 | — | • 153.9 | • |

EXAMPLE 179

Preparation of (R)—6-(trans-4'-butylcyclohexylcarbonyloxy)-2-naphthalenecarboxylic acid 1"-methylheptyl ester In 50 ml of chloroform were dissolved 1 g of trans-4-butylcyclohexylcarboxylic acid, 1.7 g of (R)-6-hydroxynapthalene-2-carboxylic acid 1'-methylheptyl ester, 1.2 g of N,N'-dicyclohexylcarbodiimide and 20 mg of 4-pyrrolidinopyridine, and the resulting mixture was then allowed to stand at room temperature for 8 hours. A secondarily produced N,N'-dicyclohexyl urea was then filtered out, and an organic layer was washed with a 2N hydrochloric acid solution, a 2N aqueous sodium hydroxide solution and water in this order.

This material was then purified by the use of a silica gel column chromatography-utilizing benzene as an eluent in order to prepare 1.2 g of the desired (R)—6-(trans-4'-butylcyclohexylcarbonyloxy)-2-naphthalenecarboxylic acid 1"-methylheptyl ester in a colorless oily state. The yield was 47%. A phase transition temperature of the thus prepared compound is set forth in Table 6. Analytical values of elements constituting this compound are closely in accord with theoretical values, as follows:

| Theoretical Value (as $C_{30}H_{42}O_4$) | | Analytical Value |
|---|---|---|
| C | 77.21% | 77.25% |
| H | 9.07% | 9.10% |

EXAMPLE 180

The same procedure as in Example 179 was repeated with the exception that trans-4-butylcyclohexylcarboxylic acid was replaced with trans-4-nonylcyclohexylcarboxylic acid in order to prepare an optically active ester compound. Its phase transition temperature which is a physical value is set forth in Table 6.

EXAMPLES 181 TO 184

The same procedure as in Example 179 was repeated with the exception that trans-4-butylcyclohexylcarboxylic acid was replaced with various trans-4-alkylcyclohexylcarboxylic acids and that (R)-6-hydroxynaphthalene-2-carboxylic acid 1'-methylheptyl ester was replaced with various optically active 6-hydroxynaphthalene-2-carboxylic acid alkyl esters in order to prepare various optically active ester compounds. Their phase transition temperatures which are physical values are set forth in Table 6.

sodium hydroxide solution and water in this order, followed by drying with anhydrous magnesium sulfate.

After the removal of methylene chloride by distillation, the resulting residue was then purified by the use of a silica gel column chromatography utilizing benzene as an eluent. The thus obtained crystal was then recrystallized out of ethanol-ethyl acetate to prepare 600 mg of the desired (s)-3-chloro-4-(6'-tetradecyloxy-2'-naphthoyloxy)benzoic acid 4''-(2'''-methylbutyloxy)phenyl ester in the state of a colorless needle crystal. The yield was 60%. A phase transition temperature of the thus prepared compound is set forth in Table 7. Analytical

TABLE 6

Structure:
$$\text{A} - \text{(naphthalene with X at position adjacent to A)} - \text{B}$$

| Example Number | Wherein A represents | Wherein B represents | X | Phase transition temperature (°C.) C SC* SA Ch I |
|---|---|---|---|---|
| 179 | $C_4H_9$— C(=O)—O— | —C(=O)—O—$\overset{*}{C}H(CH_3)C_6H_{13}$ | H | <10 |
| 180 | $C_9H_{19}$— C(=O)—O— | " | H | <10 |
| 181 | $C_7H_{15}$— C(=O)—O— | —C(=O)—O—$(CH_2)_3\overset{*}{C}H(CH_3)C_2H_5$ | H | <10 |
| 182 | $C_8H_{17}$— C(=O)—O— | " | H | <10 |
| 183 | $C_5H_{11}$— C(=O)—O— | —C(=O)—O—$(CH_2)_2\overset{*}{C}H(CH_3)$—$(CH_2)_3CH(CH_3)_2$ | H | <10 |
| 184 | $C_5H_{11}$— C(=O)—O— | —C(=O)—O—$\overset{*}{C}H(CH_3)C_3H_7$ | H | <10 |

EXAMPLE 185

Preparation of (s)-3-chloro-4-(6'-tetradecyloxy-2'-naphthoyloxy)benzoic acid 4''-(2'''-methylbutyloxy)phenyl ester (i) Preparation of (s)-3-chloro-4-hydroxybenzoic acid-4'-(2'''-methylbutyloxy)phenyl ester:

This compound was prepared from (s)-4-(2'-methylbutyloxy)phenol and 4-hydroxy-3-chlorobenzoic acid in accordance with a method described in the literature, J. Org. Chem. 40, 2998 (1975). A melting point of the product was within the range of 165.2° to 166.8° C.

(ii) In 30 ml of methylene chloride were dissolved 500 mg of 3-chloro-4-hydroxybenzoic acid-4'-(2'''-methylbutyloxy)phenyl ester obtained in the above process (i), 500 mg of 6-tetradecyloxynaphthalene-2-carboxylic acid, 300 mg of N,N'-dicyclohexylcarbodiimide and 20 mg of 4-pyrrolidinopyridine, and the resulting mixture was then allowed to stand at room temperature for 20 hours. A secondarily produced N,N'-dicyclohexyl urea was then filtered out, and an organic layer was washed with a 5% hydrochloric acid solution, a 5% aqueous values of elements constituting this compound are closely in accord with theoretical values, as follows:

| Theoretical Value (as $C_{33}H_{53}O_6Cl$) | | Analytical Value |
|---|---|---|
| C | 68.19% | 68.25% |
| H | 9.19% | 9.18% |
| Cl | 6.10% | 6.05% |

When measured at a 10° C lower temperature than an SC*-SA transition temperature, a value of a spontaneous polarization (Ps) was 2 nC/cm².

EXAMPLES 186 TO 189

The same procedure as in the process (ii) of Example 185 was repeated with the exception that 6-tetradecyloxynaphthalene-2-carboxylic acid was replaced with various 6-alkyloxynaphthalene-2-carboxylic acids in order to prepare various (s)-3-chloro-4-(6-alkyloxy-2'-naphthoyloxy)benzoic acid 4''-(2'''-methylbutyloxy)-phenyl esters. With regard to typical ones of the thus obtained products, their phase transition temperatures are set forth in Table 7.

EXAMPLES 200 TO 225

TABLE 7

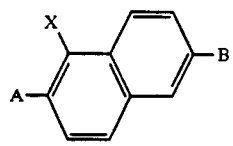

| Example Number | Wherein A represents | Wherein B represents | X | C | SC* | SA | Ch | I |
|---|---|---|---|---|---|---|---|---|
| 185 | C₁₄H₂₉O— | (see structure below) | H | • 85.2 | • 112.9 | • 141.5 | • 164.0 | • |
| 186 | C₈H₁₇O— | " | H | • 100.5 | — | (• 74.3) | • 186.4 | • |
| 187 | C₁₀H₂₁O— | " | H | • 94.6 | • 109.8 | • 121.0 | • 176.3 | • |
| 188 | C₁₂H₂₅O— | " | H | • 88.5 | • 110.3 | • 136.3 | • 169.6 | • |
| 189 | C₁₆H₃₃O— | " | H | • 92.3 | • 113.4 | • 140.5 | • 153.8 | • |

B structure:

$$-\underset{\underset{O}{\|}}{C}-O-\text{[Cl-phenyl]}-\underset{\underset{O}{\|}}{C}-O-\text{[phenyl]}-OCH_2\overset{*}{C}H(CH_3)C_2H_5$$

EXAMPLE 190

Preparation of (s)-6-octyloxynaphthalene-2-carboxylic acid 2'-methylbutyl ester

In 50 ml of toluene, 2 g of 6-octyloxynaphthalene-2-carboxylic acid and 5 ml of thionyl chloride were heated at reflux temperature for 5 hours. The used toluene and excessive thionyl chloride were distilled out under reduced pressure, and the resulting residue was then dissolved in 20 ml of toluene and was added to 10 ml of a pyridine solution containing 1 g of (s)-2-methylbutanol, followed by stirring at room temperature for 10 hours. The reaction mixture was then washed with a 20% hydrochloric acid solution, a 10% aqueous sodium hydroxide solution and water in this order. An organic layer was then dried with anhydrous magnesium sulfate. After the removal of toluene by distillation, a residual oil was then purified by the use of a silica gel column chromatography. The thus purified oil was dissolved in 5 ml of n-hexane and was then cooled at −20° C. to prepare 1.2 g of the desired (s)-6-octyloxynaphthalene-2-carboxylic acid 2'-methylbutyl ester in the state of a colorless lamellar crystal. The yield was 49%.

A phase transition temperature of the thus prepared compound is set forth in Table 8. Analytical values of elements constituting this compound are closely in accord with theoretical values, as follows:

| Theoretical Value (as C₂₄H₃₄O₃) | Analytical Value |
|---|---|
| C 77.80% | 77.85% |
| H 9.25% | 9.19% |

EXAMPLE 191 TO 199

The same procedure as in Example 190 was repeated with the exception that 6-octyloxynaphthalene-2-carboxylic acid was replaced with various 6-alkyloxynaphthalene-2-carboxylic acids or various 6-alkylnaphthalene-2-carboxylic acids, in order to prepare various optically active ester compounds. Their phase transition temperatures which are physical values are set forth in Table 8.

The same procedure as in Example 190 was repeated with the exception that 6-octyloxynaphthalene-2-carboxylic acid was replaced with various 6-alkyloxynaphthalene-2-carboxylic acids, and that (s)-2-methylbutanol was replaced with various optically active alcohols, in order to prepare various optically active ester compounds. Their phase transition temperatures which are physical values are set forth in Table 8.

EXAMPLE 226

Preparation of (s)-4-methylcaproic acid-2'-(6'-decyloxy)naphthyl ester

To a 15 ml of methylene chloride were added 600 mg of 6-decyloxy-2-naphthol, 260 mg of (s)-4-methylcaproic acid, 420 mg of N,N'-dicyclohexylcarbodiimide and 10 mg of 4-pyrrolidinopyridine, and the resulting mixture was then allowed to stand at room temperature for 2 hours. A secondarily produced N,N'-dicyclohexyl urea was then filtered out, and an organic layer was washed with a 5% hydrochloric acid solution, a 5% aqueous sodium hydroxide solution and water in this order, followed by drying with anhydrous magnesium sulfate.

After the removal of methylene chloride by distillation, the resulting residue was then purified by the use of a silica gel column chromatography utilizing benzene as an eluent in order to prepare 600 mg of the desired (s)-4-methylcaproic acid-2'-(6'-decyloxy)naphthyl ester. The yield was 73%. A phase transition temperature of the thus prepared compound is set forth in Table 8. Analytical values of elements constituting this compound are closely in accord with theoretical values, as follows:

| Theoretical Value (as C₂₇H₄₀O₃) | Analytical Value |
|---|---|
| C 78.59% | 78.40% |
| H 9.77% | 9.80% |

EXAMPLE 227 TO 229

The same procedure as in Example 226 was repeated with the exception that 6-decyloxy-2-naphthol was replaced with various 6-alkyloxy-2-naphthols, in order to prepare various optically active esters. Their phase transition temperatures which are physical values are set forth in Table 8.

EXAMPLES 230 TO 233

The same procedure as in Example 226 was repeated with the exception that 6-decyloxy-2-naphthol was replaced with various 6-alkyloxy-2-naphthols, and that (s)-4-methylcaproic acid was replaced with various optically active carboxylic acids, in order to prepare various optically active ester compounds. Their phase transition temperatures which are physical values are set forth in Table 8.

TABLE 8

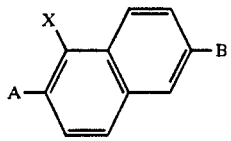

| Example Number | Wherein A represents | Wherein B represents | X | Phase transition temperature (°C.) C | I |
|---|---|---|---|---|---|
| 190 | $C_8H_{17}O-$ | $-\underset{\underset{O}{\|\|}}{C}-OCH_2\overset{CH_3}{\underset{*}{C}}HC_2H_5$ | H | • 15 | • |
| 191 | $C_6H_{13}O-$ | " | H | • 21 | • |
| 192 | $C_9H_{19}O-$ | " | H | • 17 | • |
| 193 | $C_{10}H_{21}O-$ | " | H | • 13 | • |
| 194 | $C_{11}H_{23}O-$ | " | H | • 10 | • |
| 195 | $C_{12}H_{25}O-$ | " | H | • 8 | • |
| 196 | $C_{14}H_{29}O-$ | " | H | • 12 | • |
| 197 | $C_{16}H_{33}O-$ | " | H | • 17 | • |
| 198 | $C_{18}H_{37}O-$ | " | H | • 16 | • |
| 199 | $C_8H_{17}-$ | " | H | <0 | • |
| 200 | $C_6H_{13}O-$ | $-\underset{\underset{O}{\|\|}}{C}-O\overset{CH_3}{\underset{*}{C}}HC_2H_5$ | H | • 21 | • |
| 201 | $C_8H_{17}O-$ | $-\underset{\underset{O}{\|\|}}{C}-O\overset{CH_3}{\underset{*}{C}}HC_2H_5$ | H | • 17 | • |
| 202 | $C_{10}H_{21}O-$ | " | H | • 14 | • |
| 203 | $C_{11}H_{23}O-$ | " | H | • 10 | • |
| 204 | $C_{12}H_{25}O-$ | " | H | • 14 | • |
| 205 | $C_{14}H_{29}O-$ | " | H | • 12 | • |
| 206 | $C_{16}H_{33}O-$ | " | H | • 15 | • |
| 207 | $C_{18}H_{37}O-$ | " | H | • 18 | • |
| 208 | $C_6H_{13}O-$ | $-\underset{\underset{O}{\|\|}}{C}-O\overset{CH_3}{\underset{*}{C}}HC_3H_7$ | H | • 19 | • |
| 209 | $C_8H_{17}O-$ | " | H | • 13 | • |
| 210 | $C_{10}H_{21}O-$ | " | H | • 12 | • |
| 211 | $C_{14}H_{29}O-$ | " | H | • 12 | • |
| 212 | $C_{16}H_{33}O-$ | $-\underset{\underset{O}{\|\|}}{C}-O\overset{CH_3}{\underset{*}{C}}HC_3H_7$ | H | • 14 | • |
| 213 | $C_{18}H_{37}O-$ | " | H | • 13 | • |
| 214 | $C_6H_{13}O-$ | $-\underset{\underset{O}{\|\|}}{C}-O\overset{CH_3}{\underset{*}{C}}HC_4H_9$ | H | • 20 | • |
| 215 | $C_8H_{17}O-$ | " | H | • 17 | • |
| 216 | $C_{10}H_{21}O-$ | " | H | • 14 | • |
| 217 | $C_{12}H_{25}O-$ | " | H | • 15 | • |

TABLE 8-continued

[Structure: naphthalene with X and A on one ring (positions 1,2) and B on the other ring (position 6)]

| Example Number | Wherein A represents | Wherein B represents | X | Phase transition temperature (°C.) C | I |
|---|---|---|---|---|---|
| 218 | $C_{10}H_{21}O-$ | $-\underset{\underset{O}{\|\|}}{C}-O(CH_2)_2\overset{*}{C}H(CH_3)(CH_2)_2CH=C(CH_3)_2$ | H | • 18 | • |
| 219 | $C_{10}H_{21}O-$ | $-\underset{\underset{O}{\|\|}}{C}-O-CH_2\overset{*}{C}H(OC_2H_5)CH_3$ | H | <0 | |
| 220 | $C_8H_{17}O-$ | $-\underset{\underset{O}{\|\|}}{C}-OCH_2\overset{*}{C}H(OC_3H_7)CH_3$ | H | <0 | |
| 221 | $C_8H_{17}O-$ | $-\underset{\underset{O}{\|\|}}{C}-O\overset{*}{C}H(CN)-C_8H_{17}$ | H | • 12 | • |
| 222 | $C_9H_{19}O-$ | $-\underset{\underset{O}{\|\|}}{C}-O-CH_2\overset{*}{C}H(CH_3)CO_2CH_3$ | H | <10 | |
| 223 | $C_{11}H_{23}O-$ | $-\underset{\underset{O}{\|\|}}{C}-O-\overset{*}{C}H(CH_3)-CO_2C_2H_5$ | H | <10 | |
| 224 | $C_{10}H_{21}O-$ | $-\underset{\underset{O}{\|\|}}{C}-O-\overset{*}{C}H(CH_3)-CH_2CO_2C_2H_5$ | H | <10 | |
| 225 | $C_{10}H_{21}O-$ | $-\underset{\underset{O}{\|\|}}{C}-O\overset{*}{C}H(CH_3)CH_2CO_2C_4H_9$ | H | <10 | |
| 226 | $C_{10}H_{21}O-$ | $-O\underset{\underset{O}{\|\|}}{C}-CH_2CH_2\overset{*}{C}H(CH_3)C_2H_5$ | H | • 34.9 | • |
| 227 | $C_8H_{17}O-$ | " | H | • 31.0 | • |
| 228 | $C_{12}H_{25}O-$ | " | H | • 30.3 | • |
| 229 | $C_{14}H_{29}O-$ | " | H | • 32.0 | • |
| 230 | $C_8H_{17}O-$ | $-O\underset{\underset{O}{\|\|}}{C}-\overset{*}{C}H(CH_3)C_2H_5$ | H | • 51.5 | • |
| 231 | $C_{10}H_{21}O-$ | " | H | • 46.5 | • |
| 232 | $C_8H_{17}O-$ | $-O\underset{\underset{O}{\|\|}}{C}-\overset{*}{C}H(Cl)-\overset{*}{C}H(CH_3)C_2H_5$ | H | • 27.5 | • |

TABLE 8-continued

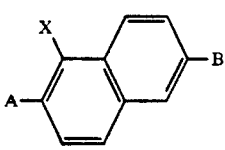

| Example Number | Wherein A represents | Wherein B represents | X | Phase transition temperature (°C.) C | I |
|---|---|---|---|---|---|
| 233 | C$_{10}$H$_{21}$O— | —OC(=O)—CH(Br)—CH(CH$_3$)C$_2$H$_5$ | H | • 26.2 | • |

EXAMPLE 234

A liquid crystal composition was prepared from the following three liquid crystal compounds of the present invention C$_{10}$H$_{21}$O—⟨⟩—C(=O)—O—⟨naphthalene⟩—C(=O)—O—*CH(CH$_3$)CH$_2$C$_2$H$_5$ C$_{10}$H$_{21}$O—⟨⟩—C(=O)—O—⟨naphthalene⟩—C(=O)—O—*CH(CH$_3$)C$_6$H$_{13}$ C$_8$H$_{17}$O—⟨⟩—⟨⟩—C(=O)—O—⟨naphthalene⟩—C(=O)—O—*CH(CH$_3$)C$_6$H$_{13}$ in amounts of 4 parts, respectively.

The thus prepared liquid crystal composition was indicative of an SC* phase at a temperature up to 47° C., an SA phase within the range of 47° to 95° C., and the state of an isotropic liquid at a higher temperature. Therefore, this composition is desirable as a material for display elements used in the vicinity of room temperature.

This composition was afterward placed in a cell having a pair of electrodes a space between which was 5 μm and which had been subjected to a rhombic vapor deposition of silica. The liquid crystal cell was then put between two light polarizers disposed in the relation of crossed Nicols, and an alternating voltage of 10 V having a low frequency (1 Hz) was applied to the cell. At this time, a clear switching phenomenon was observed and a contrast of the cell was very sharp, and in addition, a response speed was fairly high (80 μsec). In this case, a value of a spontaneous polarization (Ps) was 42 nC/cm$^2$.

EXAMPLE 235

A liquid crystal composition was prepared from the following three liquid crystal compounds of the present invention C$_{10}$H$_{21}$O—⟨F⟩—C(=O)—O—⟨naphthalene⟩—C(=O)—O—*CH(CH$_3$)CH$_2$C$_2$H$_5$ C$_{10}$H$_{21}$O—⟨F⟩—C(=O)—O—⟨naphthalene⟩—C(=O)—O—*CH(CH$_3$)C$_6$H$_{13}$ C$_{10}$H$_{21}$O—⟨⟩—C(=O)—O—⟨naphthalene⟩—C(=O)—O—*CH(CH$_3$)C$_6$H$_{13}$ in amounts of 2 parts, respectively.

The thus prepared liquid crystal composition was indicative of an SC* phase at a temperature up to 40° C., an SA phase within the range of 40° to 67° C., and the state of an isotropic liquid at a higher temperature. Therefore, this composition is desirable as a material for display elements used in the vicinity of room temperature.

This composition was afterward placed in a cell having a pair of electrodes a space between which was 5 μm and which had been subjected to a rhombic vapor deposition of silica. The liquid crystal cell was then put between two light polarizers disposed in the relation of crossed Nicols, and an alternating voltage of 10 V having a low frequency (1 Hz) was applied to the cell. At this time, a clear switching phenomenon was observed and a contrast on the cell was very sharp, and in addition a response speed was fairly high (100 μsec). In this case, a value of a spontaneous polarization (Ps) was 38 nC/cm$^2$.

EXAMPLE 236

A liquid crystal composition was prepared from a known liquid crystal compound having the formula

C$_7$H$_{15}$O—⟨⟩—⟨⟩—C(=O)—O—⟨⟩—C(=O)—OCH$_2$*CH(CH$_3$)C$_2$H$_5$ (in this compound, a phase transition temperature was a crystal $\xrightarrow{72°\ C.}$ SC* $\xrightarrow{137°\ C.}$ -continued

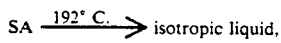

and a response speed was 1 msec) in an amount of 10 parts and a compound of the present invention having the formula

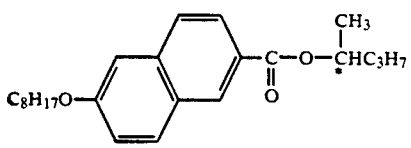

in an amount of 1 part.

The thus prepared composition was indicative of the following phase transition temperature:

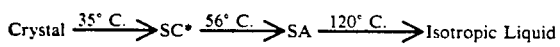

Similarly, this composition was placed in the same cell as in Example 234 and a response speed was then measured. It was 500 μsec, and this fact indicates that the conventional compound was remarkably improved in point of the response speed.

EXAMPLE 237

Following the same procedure as in Example 236, a composition was prepared by mixing a compound of the present invention having the formula

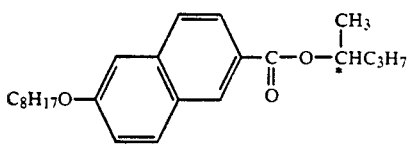

in an amount of 1 part with a liquid crystal compound (response speed 1 msec) of the present invention having the formula

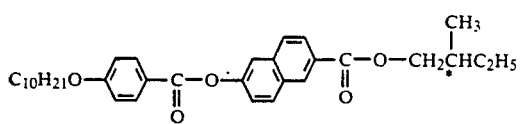

in an amount of 10 parts. The thus prepared composition had the following phase transition temperature:

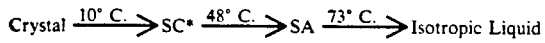

Therefore, the composition can work at room temperature. Further, a response speed of the composition was 200 μsec which was much higher than that of the mixture in Example 236.

As is apparent from the foregoing, among the compounds of the present invention, even ones which do not show any liquid crystal phase can work at a temperature in the vicinity of room temperature and can thus be considered to be useful to obtain liquid crystal compositions having a high response speed.

EXAMPLE 238

The compound prepared in Example 9 and known optically active 4-1 -decyloxybenzylidene-4'-amino-2"-methylbuthyl cinnamate (DOBAMBC) having the chemical structure 1 in Table 1 were each placed in a sample tube, and each sample was allowed to stand in an atmosphere at a temperature 60° C. and a humidity of 90% for 40 hours, and before and after this standing step, the variation of an SC*-SA transition temperature was measured.

The SC*-SA transition temperature of DOBAMBC dropped as much as 20° C. of from 95° to 75° C., whereas that of the compound prepared in Example 9 did not vary at all. This fact indicates that the latter compound is very stable to the moisture.

EXAMPLE 239

The compound prepared in Example 9 and the known DOBAMBC were each placed in a glass tube, and light irradiation was carried out for 30 hours by the use of a carbon arc. Before and after the irradiation step, the variation of an SC*-SA transition temperature was measured.

The SC*-SA transition temperature of DOBAMBC dropped as much as 20° C. of from 95° C. to 75° C., whereas that of the compound prepared in Example 9 did not vary at all. This fact indicates that the latter compound is very stable to the light.

What is claimed is:

1. Optically active naphthalene derivatives according to formula II:

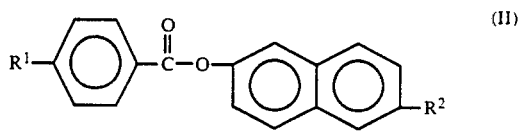

wherein $R^1$ is $C_6-C_{14}$ alkoxy and $R^2$ is selected from the group consisting of:

wherein $R^3$ is $C_1-C_4$ alkyl.

2. The naphthalene derivative according to claim 1, wherein $R^1$ is $C_8-C_{12}$ alkoxy and $R^3$ is ethyl.

3. The naphthalene derivative according to claim 1, wherein $R^1$ is $C_8-C_{12}$ alkoxy and $R^3$ is propyl.

* * * * *

UNITED STATES PATENT AND TRADEMARK OFFICE
CERTIFICATE OF CORRECTION

PATENT NO. : 5,072,021
DATED : December 10, 1991
INVENTOR(S) : Masakatsu NAKATSUKA et al It is certified that error appears in the above-indentified patent and that said Letters Patent is hereby corrected as shown below:

On the Title page, Item [54], "OPTICAL" should read
--OPTICALLY--.

Signed and Sealed this

Twenty-ninth Day of June, 1993

Attest:

MICHAEL K. KIRK

Attesting Officer

Acting Commissioner of Patents and Trademarks